United States Patent

Leppard et al.

Patent Number: 5,723,512
Date of Patent: Mar. 3, 1998

[54] DIMERIC BISACYLPHOSPHINES, OXIDES AND SULFIDES

[75] Inventors: David G. Leppard, Marly, Switzerland; Manfred Köhler, Freiburg, Germany

[73] Assignee: Ciba Specialty Chemicals Corporation, Tarrytown, N.Y.

[21] Appl. No.: 669,807

[22] Filed: Jun. 27, 1996

Related U.S. Application Data

[63] Continuation of Ser. No. 392,563, Feb. 23, 1995, abandoned.

[30] Foreign Application Priority Data

Mar. 2, 1994 [CH] Switzerland ................... 614/94

[51] Int. Cl.$^6$ ............... C07F 9/53; C07F 9/02; C08F 2/50; C08K 3/22
[52] U.S. Cl. ............... 522/55; 522/64; 522/17; 522/18; 522/103; 522/81; 522/53; 522/63; 568/14; 568/15
[58] Field of Search ............... 522/17, 55, 64, 522/18, 63, 81, 103, 53; 568/14, 15

[56] References Cited

U.S. PATENT DOCUMENTS

| | | | |
|---|---|---|---|
| 4,737,593 | 4/1988 | Ellrich et al. | 568/15 |
| 4,792,632 | 12/1988 | Ellrich et al. | 568/15 |
| 5,436,280 | 7/1995 | Medsker, II et al. | 522/64 |

OTHER PUBLICATIONS

Chem. Abstracts 90: 87589d Organometallics p. 639 vol. 90 (1979).
Derwent Abst. 92-243582/30, 1991.
Chem Abst. 117:214590a vol. 117, 1992.
Derwent Abst. 92-243583/30, 1991.
Chem. Abst. 118: 40894f, 1993.
Chem. Abst. 119: 74134u, 1994.
Derwent Abst. 92-33567/41, 1991.
Zhurnal Obshchei Khimii, vol. 36, No. 1, 79–80 (1966).
Z. Naturforsch. 33b, 1457–1469 (1978).

*Primary Examiner*—Susan W. Berman
*Attorney, Agent, or Firm*—Michele A. Kovaleski; Victoria M. Malia

[57] ABSTRACT

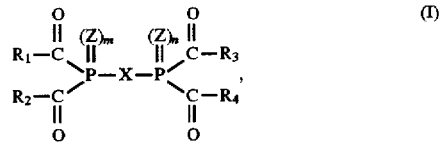

in which

Z is oxygen or sulfur, n and m are independently of one another 0 or 1, $R_1$, $R_2$, $R_3$, $R_4$ and X are as defined in claim 1, are suitable as photoinitiators for the polymerization of ethylenically unsaturated compounds.

10 Claims, No Drawings

DIMERIC BISACYLPHOSPHINES, OXIDES AND SULFIDES

This application is a continuation of application Ser. No. 08/392,563, filed Feb. 23, 1995, now abandoned.

The invention relates to dimeric bisacylphosphine, bisacylphosphine sulfide and bisacylphosphine oxide compounds, to compositions comprising these compounds and to the use of the compounds as photoinitiators for the photopolymerization of ethylenically unsaturated compounds.

The use of bisacylphosphine oxides as photoinitiators is known from EP-A-184 095. Bisacylphosphines are described in the EP-A-495 751. Bisacylphosphine sulfides are disclosed in EP-A-495 752. Dimeric monoacylphosphine oxides as photoinitiators are described in Chemical Abstracts 119(8), 74134u. E. Lindner and G. Vordermeier report in Z. Naturforsch. 33b, 1457–1469 (1978) on the behaviour of bifunctional acyl(diorganyl)phosphanes with respect to oxygen. The acylphosphine oxides disclosed in this reference are also dimeric monoacylphosphine oxide compounds. E. L. Gefter and I. A. Rogacheva disclosed the synthesis of ethylene glycol esters of phosphates in Zhurnal Obshchei Khimii, Vol. 36, No. 1, 79–81 (1966). The compounds described in this reference are also dimeric monoacylphosphine oxides.

For the extensive range of applications of photoinitiators, there continues to be a need for effective compounds.

It has been found that dimeric bisacylphosphines, bisacylphosphine sulfides and bisacylphosphine oxides are effective photoinitiators.

The invention therefore relates to compounds of the formula I

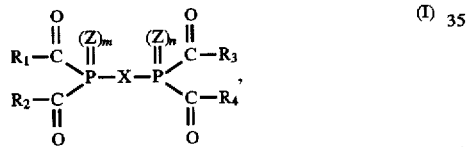

in which

Z is oxygen or sulfur, n and m are independently of one another 0 or 1, $R_1$, $R_2$, $R_3$ and $R_4$ independently of one another are $C_1$–$C_{20}$alkyl, cyclopropyl, cyclopentyl, cyclohexyl, $C_2$–$C_8$alkenyl, phenyl which is unsubstituted or is substituted one to four times by $C_1$–$C_{12}$alkyl, $C_1$–$C_{12}$alkoxy, $C_1$–$C_6$alkylthio and/or halogen, naphthyl which is unsubstituted or is substituted one to four times by $C_1$–$C_{12}$alkyl, $C_1$–$C_{12}$alkoxy, $C_1$–$C_6$alkylthio and/or halogen, biphenyl which is unsubstituted or is substituted one to four times by $C_1$–$C_{12}$alkyl, $C_1$–$C_{12}$alkoxy, $C_1$–$C_6$alkylthio and/or halogen, or $R_1$, $R_2$, $R_3$ and $R_4$ independently of one another are a 5- or 6-membered heterocyclic ring which contains O, S or N, or $R_1$ and $R_2$ or/and $R_3$ and $R_4$ are linked to form a ring containing 4 to 10 carbon atoms which is unsubstituted or is substituted by 1 to 6 $C_1$–$C_4$alkyl groups, X is linear or branched $C_1$–$C_{18}$alkylene, is $C_2$–$C_{18}$alkylene which is interrupted one or more times by —O—, —S—, —NR$_5$—, —P(O)R$_6$— or —SO$_2$—, or is $C_1$–$C_6$alkylene which is substituted by Cl, F, $C_1$–$C_4$alkoxy, COOR$_7$, phenyl, $C_1$–$C_4$alkylphenyl, $C_1$–$C_4$alkylnaphthyl phenyl-$C_1$–$C_4$alkyl, naphthyl-$C_1$–$C_4$alkyl, phenyl-$C_1$–$C_4$alkoxy, naphthyl-$C_1$–$C_4$alkoxy, $C_1$–$C_4$alkoxy-$C_1$–$C_4$alkoxy and/or CN, or X is $C_2$–$C_8$alkylene which is substituted by one or two groups of the formula G

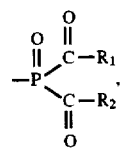

or X is a group of the formula (II), (III), (IV), (V), (VI), (VII), (VIII), (IX) or (X)

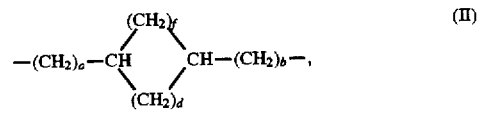

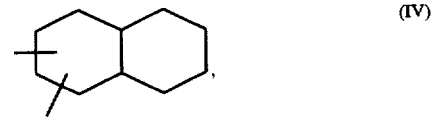

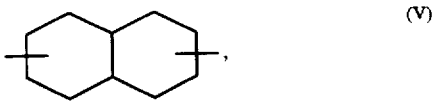

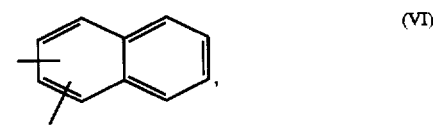

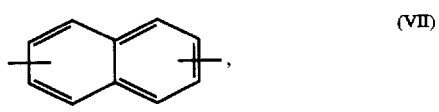

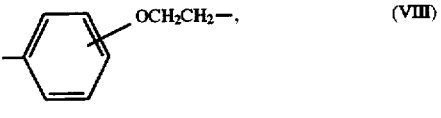

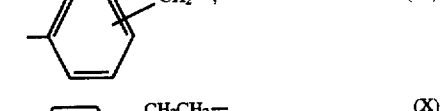

in which a and b independently of one another are 0 or 1, the sum of d and f is 3 to 8, with neither d nor f being 0, or X is a group —CH$_2$—CH=CH—CH$_2$— or —CH$_2$—C≡C—CH$_2$—, or X is phenylene which is unsubstituted or is substituted one to three times by Cl, F, $C_1$–$C_4$alkyl and/or $C_1$–$C_4$alkoxy, or is xylylene,

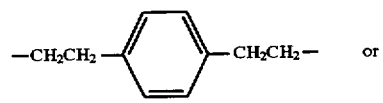

or

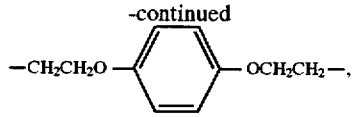

or X is phenylene which is substituted by one or two groups G and which may also be substituted one to three times by Cl, F, C$_1$–C$_4$alkyl and/or C$_1$–C$_4$alkoxy, or X is a group of the formula (XI), (XII), (XIII) or (XIV)

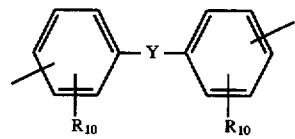 (XI)

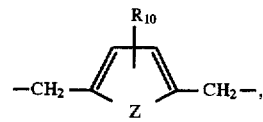 (XII)

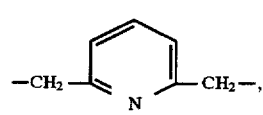 (XIII)

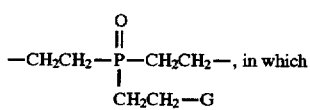 (XIV)

Z and G are as defined above and

Y is a single bond, —CR$_8$R$_9$—, —O—, —NR$_5$—, —S—, —SO$_2$—, —(CH$_2$)$_p$— or —CH=CH—, p is a number from 2 to 12, R$_5$ is hydrogen, C$_1$–C$_{12}$alkyl or phenyl, R$_6$ is C$_1$–C$_4$alkyl or phenyl, R$_7$ is C$_1$–C$_{12}$alkyl, C$_2$–C$_{18}$alkyl which is interrupted by one or more O atoms, or is benzyl, phenyl, cyclopentyl or cyclohexyl, and R$_8$ is hydrogen, methyl or ethyl, R$_9$ is hydrogen or C$_1$–C$_4$alkyl, and R$_{10}$ is C$_1$–C$_4$alkyl, C$_1$–C$_4$alkoxy or halogen.

C$_1$–C$_{20}$Alkyl R$_1$, R$_2$, R$_3$ and R$_4$ are linear or branched radicals and are for example methyl, ethyl, propyl, isopropyl, n-butyl, sec-butyl, iso-butyl, tert-butyl, pentyl, hexyl, heptyl, 2,4,4-trimethylpentyl, 2-ethylhexyl, octyl, nonyl, decyl, dodecyl, tetradecyl, heptadecyl, octadecyl, nonadecyl or eicosyl. For example, R$_1$, R$_2$, R$_3$ and R$_4$ are C$_1$–C$_{18}$alkyl, especially C$_1$–C$_{12}$alkyl. Secondary or tertiary C$_3$–C$_{18}$alkyl or C$_3$–C$_{12}$alkyl are preferred, especially tert-C$_4$–C$_8$alkyl.

C$_1$–C$_{12}$Alkyl R$_5$ and R$_7$ and C$_1$–C$_4$alkyl R$_6$, R$_9$ and R$_{10}$ are as defined for R$_1$, R$_2$, R$_3$ and R$_4$ except for the corresponding number of carbon atoms. Examples of R$_5$ and R$_7$ are C$_1$–C$_8$alkyl, especially C$_1$–C$_4$alkyl. R$_6$ is in particular methyl.

C$_2$–C$_8$Alkenyl R$_1$, R$_2$, R$_3$ and R$_4$ are for example allyl, methallyl, 1,1-dimethylallyl, butenyl, hexenyl or octenyl, especially allyl.

C$_1$–C$_4$Alkoxy R$_{10}$ is for example methoxy, ethoxy, n-propoxy, isopropoxy, n-butoxy, isobutoxy, s-butoxy or t-butoxy, especially methoxy.

Substituted phenyl, naphthyl or biphenyl is substituted one to four times, for example once, twice or three times, in particular two or three times.

Substituted phenyl, naphthyl or biphenyl R$_1$, R$_2$, R$_3$ and R$_4$ are for example substituted by linear or branched C$_1$–C$_{12}$alkyl such as methyl, ethyl, n-propyl, i-propyl, n-butyl, i-butyl, s-butyl, t-butyl, pentyl, hexyl, heptyl, octyl, nonyl, decyl or dodecyl or by linear or branched C$_1$–C$_{12}$alkoxy such as methoxy, ethoxy, n-propoxy, isopropoxy, n-butoxy, isobutoxy, s-butoxy, t-butoxy, hexyloxy, octyloxy, nonyloxy, decyloxy or dodecyloxy or by linear or branched C$_1$–C$_6$alkylthio such as methylthio, ethylthio, n-propylthio, isopropylthio, n-butylthio, isobutylthio, s-butylthio, t-butylthio, pentylthio or hexylthio or by halogen such as fluorine, chlorine, bromine or iodine. Preferred substituents for phenyl, naphthyl and biphenyl R$_1$, R$_2$, R$_3$ and R$_4$ are C$_1$–C$_4$alkyl, especially methyl, C$_1$–C$_4$alkoxy, especially methoxy, and chlorine. Particularly preferred examples of R$_1$, R$_2$, R$_3$ and R$_4$ are 2,4,6-trimethylphenyl, 2,6-dichlorophenyl, 2,6-dimethylphenyl or 2,6-dimethoxyphenyl.

R$_1$, R$_2$, R$_3$ and R$_4$ as 5- or 6-membered heterocyclic rings containing O, S or N are for example furyl, thienyl, pyrrolyl or pyridyl. The heterocyclic radicals mentioned may be substituted one or more times, for example once or twice, by linear or branched C$_1$–C$_6$alkyl such as methyl, ethyl, propyl, butyl, pentyl or hexyl, especially C$_1$–C$_4$alkyl. Examples are dimethylpyridyl, dimethylpyrrolyl or methylfuryl.

R$_1$ and R$_2$ or/and R$_3$ and R$_4$ linked to form a ring containing 4–10 carbon atoms may include the P atom and the two carbonyl C atoms to which R$_1$ and R$_2$ and/or R$_3$ and R$_4$ are attached. An example of the resulting structural elements is

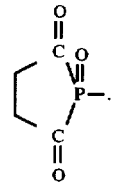

The ring may, however, also be adjacent to the two carbonyl carbon atom. In such cases the ring may be aliphatic or aromatic and is for example cyclohexyl or benzyl. The following structural units, for example, are then involved:

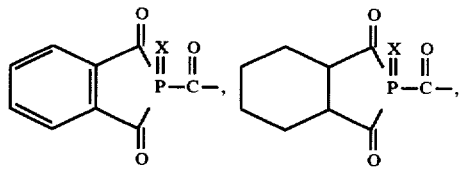

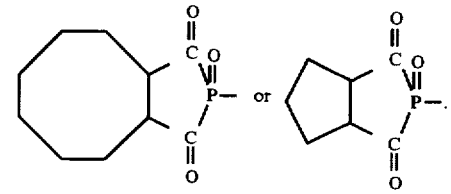

If these radicals are substituted by C$_1$–C$_6$alkyl the substituent radicals are linear or branched and are for example methyl, ethyl, n-propyl, isopropyl, n-butyl, isobutyl, s-butyl, t-butyl, pentyl or hexyl, preferably methyl.

Y as —(CH$_2$)$_p$— is preferably —CH$_2$CH$_2$—.

C$_1$–C$_{18}$Alkylene X is linear or branched alkylene such as methylene, ethylene, propylene, isopropylene, n-butylene, sec-butylene, isobutylene, tert-butylene, pentylene, hexylene, heptylene, octylene, nonylene, decylene, dodecylene, tetradecylene, heptadecylene or octadecylene. X is in particular $C_1$–$C_{12}$alkylene, such as ethylene, decylene,

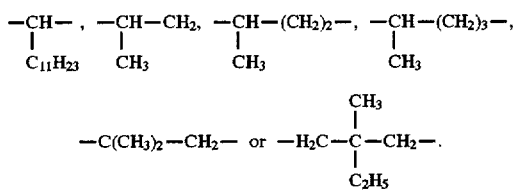

$C_2$–$C_{18}$Alkylene X interrupted by —O—, —S—, —$NR_5$—, —$P(O)R_6$— or —$SO_2$— results in structural units such as —$CH_2$—O—$CH_2$—, —$CH_2CH_2$—O—$CH_2CH_2$—, —$[CH_2CH_2O]_y$—, where y=1–9, —($CH_2CH_2O)_7CH_2CH_2$—, —$CH_2$—$CH(CH_3)$—O—$CH_2$—$CH(CH_3)$—, —$CH_2$—S—$CH_2$—, —$CH_2CH_2$—S—$CH_2CH_2$—, —$CH_2CH_2CH_2$—S—$CH_2CH_2CH_2$—, —$(CH_2)_3$—S—$(CH_2)_3$—S—$(CH_2)_3$—, —$CH_2$—$(NR_5)$—$CH_2$—, —$CH_2CH_2$—$(NR_5)$—$CH_2CH_2$—, —$CH_2$—$(P(O)R_6)$—$CH_2$—, —$CH_2CH_2$—$(P(O)R_6)$—$CH_2CH_2$—,

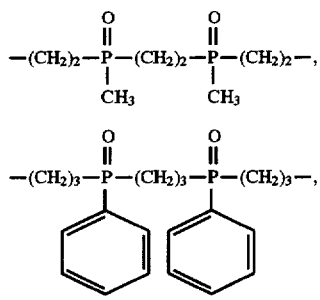

—$CH_2$—$SO_2$—$CH_2$— or —$CH_2CH_2$—$SO_2$—$CH_2CH_2$—.

$C_1$–$C_4$Alkoxy substituents are for example methoxy, ethoxy, propoxy or butoxy, especially methoxy. $C_1$–$C_6$Alkylene substituted by $C_1$–$C_4$alkoxy or —$COOR_7$ is for example

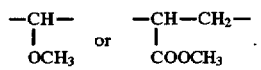

$C_1$–$C_4$Alkylphenyl is for example tolyl, xylyl, mesityl, ethylphenyl or diethylphenyl, preferably tolyl or mesityl.

$C_1$–$C_4$Alkylnaphthyl is naphthyl substituted by methyl, ethyl and/or propyl or butyl.

Phenyl-$C_1$–$C_4$alkyl is for example benzyl, phenylethyl, α-methylbenzyl or α,α-dimethylbenzyl, especially benzyl.

Naphthyl-$C_1$–$C_4$alkyl is for example naphthylmethyl, naphthylethyl, naphthyl(1-methyl)eth-1-yl or naphthyl(1,1-dimethyl)eth-1-yl, especially naphthylmethyl.

$C_1$–$C_4$Alkylphenyl-$C_1$–$C_4$alkyl is for example 2,4,6-trimethylbenzyl, 2,6-dimethylbenzyl, 2,4,6-trimethylphenylethyl, 4-methylbenzyl or 4-ethylbenzyl, especially 2,4,6-trimethylbenzyl.

Phenyl-$C_1$–$C_4$alkoxy is for example benzyloxy, phenylethyloxy, α-methylbenzyloxy or α,α-dimethylbenzyloxy, especially benzyloxy.

Naphthyl-$C_1$–$C_4$alkoxy is for example naphthylmethyloxy or naphthylethyloxy.

$C_1$–$C_4$Alkoxy-$C_1$–$C_4$alkoxy is for example methoxyethoxy, methoxypropoxy, methoxybutoxy, ethoxymethoxy, ethoxyethoxy, ethoxypropoxy, ethoxybutoxy, propoxymethoxy, propoxyethoxy, propoxypropoxy, propoxybutoxy, butoxymethoxy, butoxyethoxy, butoxypropoxy or butoxybutoxy, especially methoxyethoxy and ethoxyethoxy.

$C_2$–$C_8$Alkylene substituted by one or two groups (G) is for example:

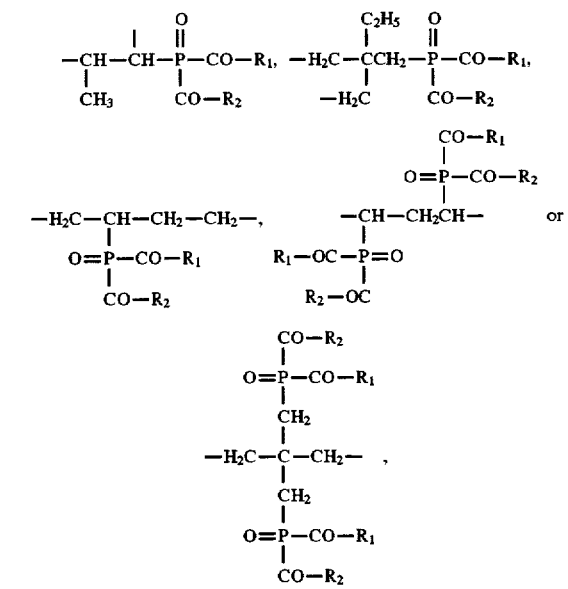

in which $R_1$ and $R_2$ are as defined above.

X as $C_1$–$C_{18}$alkylene substituted by Cl, F, phenyl, $C_1$–$C_4$alkoxy-$C_1$–$C_4$alkoxy, phenyl-$C_1$–$C_4$alkyl, phenyl-$C_1$–$C_4$alkoxy and $C_1$–$C_4$alkylphenyl-$C_1$–$C_4$alkyl is for example: —$CF_2$—$CF_2$—, —$CCl_2$—$CF_2$—,

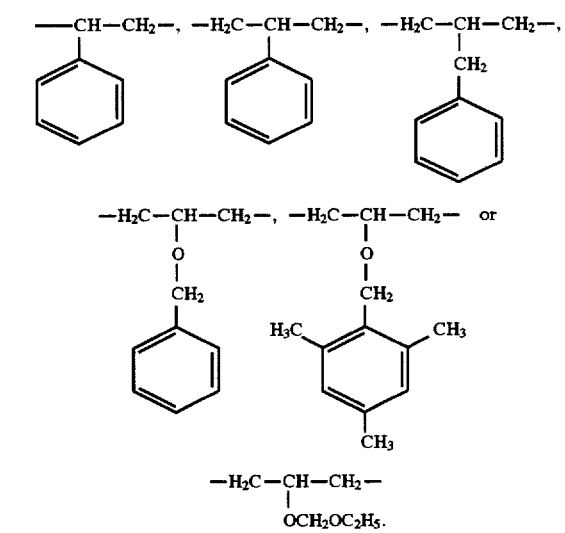

Examples of groups of the formula (II) in which the sum of d and f is from 3 to 8 are:

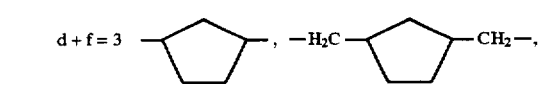

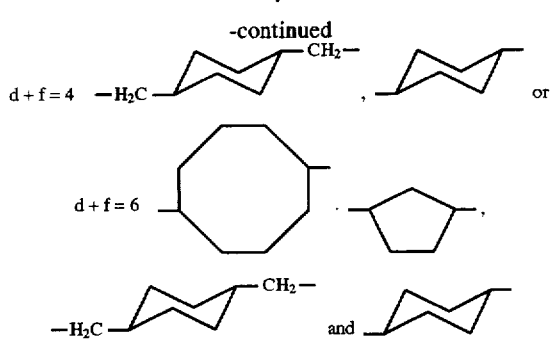

are preferred.

$C_1-C_4$Alkyl and $C_1-C_4$alkoxy substituents for phenylene or xylylene are for example methyl, ethyl, n-propyl, isopropyl, n-butyl, tert-butyl, isobutyl, s-butyl, methoxy, ethoxy, propoxy or butoxy, especially methyl and methoxy. Examples of unsubstituted and substituted phenylene or xylylene are

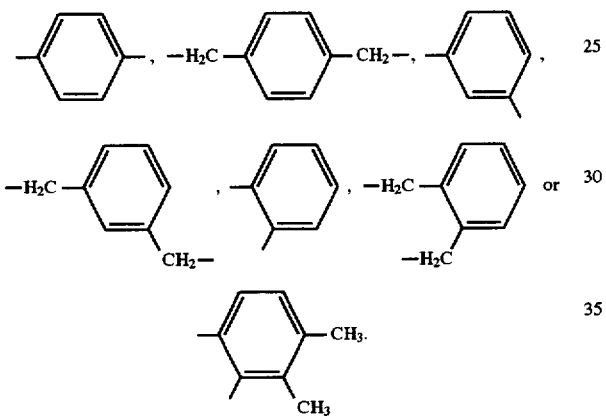

Examples of phenylene substituted by G are:

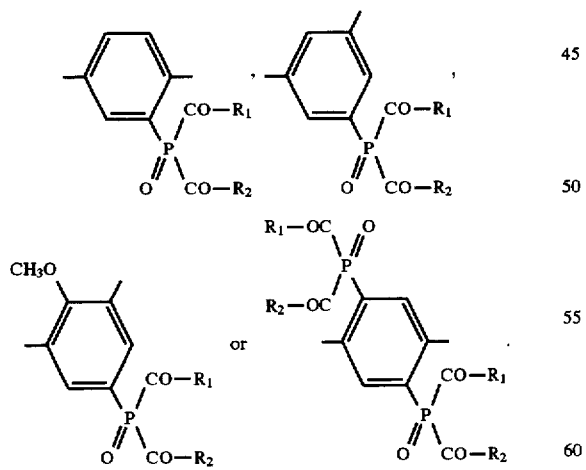

The ring in the formula XII is either a thiophene or a furan ring.

Examples of groups of the formulae (V), (VI), (VII) and (X) are

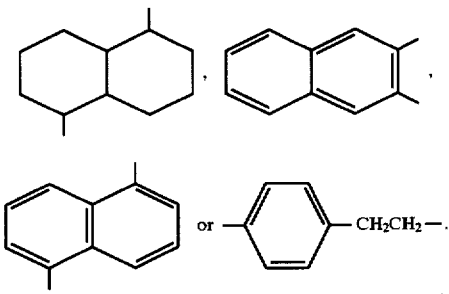

Examples of the group of the formula (XI) are

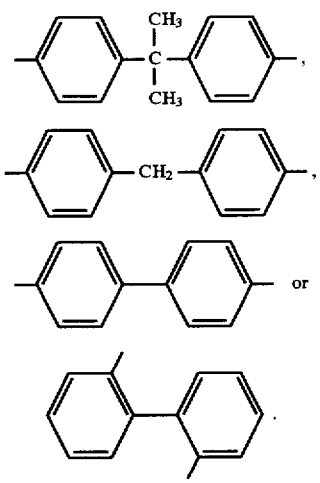

$C_1-C_{12}$Alkyl $R_8$ and $R_7$, $C_1-C_4$alkyl $R_9$ may be as defined for $R_1$, $R_2$, $R_3$ and $R_4$ except for the corresponding number of carbon atoms.

$R_7$ as $C_2-C_{18}$alkyl interrupted by O is for example methoxymethyl, ethoxymethyl, methoxyethyl, ethoxyethyl or a structural unit of the formula $CH_3CH_2O-[CH_2CH_2O]_y-$, where $y=1-14$, especially methoxymethyl.

Halogen is fluorine, chlorine, bromine and iodine, for example bromine and chlorine and especially chlorine.

Preferred compounds of the formula I are those in which $R_1$, $R_2$, $R_3$ and $R_4$ are tert-$C_4-C_8$alkyl, cyclopentyl, cyclohexyl or a radical

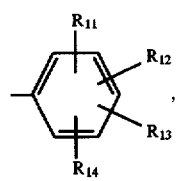

in which $R_{11}$ is $C_1-C_8$alkyl, $C_1-C_8$alkoxy, $C_1-C_4$alkylthio or halogen, $R_{12}$, $R_{13}$ and $R_{14}$ independently of one another are hydrogen, $C_1-C_8$alkyl, $C_1-C_8$alkoxy, $C_1-C_4$alkylthio or halogen, or $R_1$, $R_2$, $R_3$ and $R_4$ are naphthyl which is unsubstituted or is substituted one to four times by $C_1-C_8$alkyl, $C_1-C_8$alkoxy, $C_1-C_4$alkylthio and/or halogen, or are biphenyl which is unsubstituted or is substituted one to four times by $C_1-C_8$alkyl, $C_1-C_8$alkoxy, $C_1-C_4$alkylthio and/or halogen, or $R_1$, $R_2$, $R_3$ and $R_4$ independently of one another are a 5- or 6-membered heterocyclic ring containing O, S or N, or $R_1$ and $R_2$ and $R_3$ and $R_4$ are linked to form a benzene ring, in which case $R_1$ and $R_2$, and $R_3$ $R_4$, are in each case ortho to one another, X is linear or branched $C_1$–$C_{18}$alkylene, is $C_4$–$C_{18}$alkylene which is interrupted one or more times by —O—, —S— or —SO$_2$—, or is $C_1$–$C_4$alkylene which is substituted by Cl, F, methoxy, COOCH$_3$, phenyl, $C_1$–$C_4$alkyl-phenyl or phenyl-$C_1$–$C_4$alkyl, or X is $C_2$–$C_8$alkylene which is substituted by one or two groups of the formula G, or X is a group of the formula (II), (IX), (X) or (XI), or X is s group —CH$_2$—CH=CH—CH$_2$— or —CH$_2$—C≡C—CH$_2$—, or X is phenylene which is unsubstituted or is substituted one to three times by Cl, F, $C_1$–$C_4$alkyl and/or $C_1$–$C_4$alkoxy, or is xylylene,

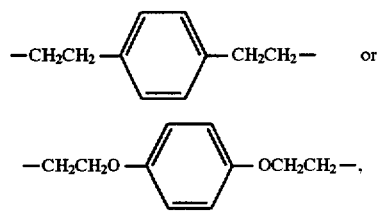

or X is phenylene substituted by one or two groups G, or X is a group of the formula (XIV), Y is a single bond, —CR$_8$R$_9$—, —O—, —S—, —SO$_2$—, —CH$_2$CH$_2$— or —CH=CH— and $R_8$ and $R_9$ independently of one another are hydrogen of methyl.

Further compounds of the formula I which are of interest are those in which $R_1$, $R_2$, $R_3$ and $R_4$ are a radical

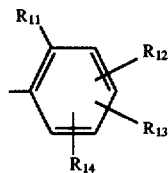

in which $R_{11}$ is $C_1$–$C_4$alkyl, $C_1$–$C_4$alkoxy, $C_1$–$C_4$alkylthio or halogen, $R_{12}$, $R_{13}$ and $R_{14}$ independently of one another are hydrogen, $C_1$–$C_4$alkyl, $C_1$–$C_4$alkoxy, $C_1$–$C_4$alkylthio or halogen, or $R_1$, $R_2$, $R_3$ and $R_4$ are naphthyl which is unsubstituted or is substituted one to four times by $C_1$–$C_4$alkyl, $C_1$–$C_4$alkoxy, $C_1$–$C_2$alkylthio and/or halogen, or are biphenyl which is unsubstituted or is substituted one to four times by $C_1$–$C_4$alkyl, $C_1$–$C_4$alkoxy, $C_1$–$C_2$alkylthio and/or halogen, X is linear or branched $C_1$–$C_{12}$alkylene, or is $C_4$–$C_{18}$alkylene which is interrupted one or more times by —O— or —S—, or is $C_1$–$C_4$alkylene which is substituted by Cl, F, methoxy, phenyl or benzyl, or X is $C_2$–$C_8$alkylene which is substituted by one or two groups of the formula G or X is a group

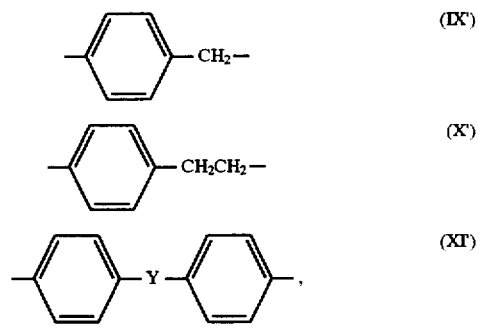

or is a group of the formula (IX'), (X') or (XI')

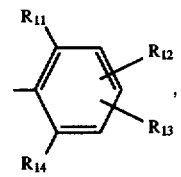

or X is a group —CH$_2$—CH=CH—CH$_2$—, or X is phenylene which is unsubstituted or is substituted one to three times by Cl, F, $C_1$–$C_4$alkyl and/or $C_1$–$C_4$alkoxy, or is xylylene, or X is phenylene which is substituted by one or two groups G, or X is a group of the formula (XIV), Y is a single bond, —CR$_8$R$_9$—, —O—, —S— or —CH$_2$CH$_2$—, and $R_8$ and $R_9$ independently of one another are hydrogen or methyl.

Notable compounds of the formula I are those in which $R_1$, $R_2$, $R_3$ and $R_4$ are a radical,

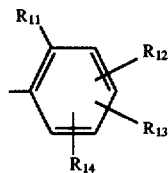

in which $R_{11}$ and $R_{14}$ independently of one another are $C_1$–$C_4$alkyl, $C_1$–$C_4$alkoxy, $C_1$–$C_2$alkylthio or halogen, $R_{12}$ and $R_{13}$ independently of one another are hydrogen, $C_1$–$C_4$alkyl, $C_1$–$C_4$alkoxy, $C_1$–$C_2$alkylthio or halogen, X is linear or branched $C_1$–$C_{12}$alkylene, $C_4$–$C_{14}$alkylene which is interrupted one or more times by —O— or —S—, or $C_2$–$C_8$alkylene which is substituted by one or two groups of the formula G, or is a group

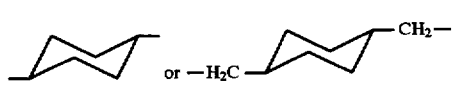

or a group of the formula (XI'), or X is a group —CH$_2$—CH=CH—CH$_2$—, phenylene or xylylene or is phenylene substituted by one or two groups G, or X is a group of the formula (XIV), Y is a single bond or —CR$_8$R$_9$—, and $R_8$ and $R_9$ independently of one another are hydrogen or methyl.

Further preferred compounds of the formula I are those in which $R_1$, $R_2$, $R_3$ and $R_4$ are a group of the formula

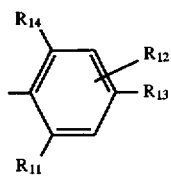

in which $R_{11}$ and $R_{14}$ independently of one another are $C_1$–$C_4$alkyl, especially methyl, methoxy or chlorine, $R_{12}$ and $R_{13}$ independently of one another are $C_1$–$C_4$alkyl, especially methyl, $C_1$–$C_4$alkoxy, chlorine or hydrogen, X is linear or branched $C_1$–$C_{12}$alkylene, $C_4$–$C_8$alkylene which is interrupted one or more times by —O—, or $C_3$–$C_6$alkylene which is substituted by one or two groups of the formula G, or X is a group —CH$_2$—CH=CH—CH$_2$— or is phenylene which is unsubstituted or is substituted by one or two groups of the formula G, or X is a group

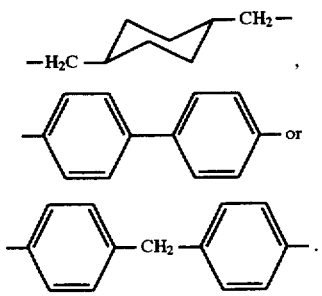

Particular preference is given to those compounds of the formula I in which $R_1$, $R_2$, $R_3$ and $R_4$ are a group of the formula

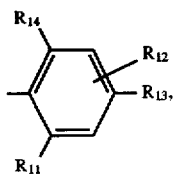

in which $R_{11}$ and $R_{14}$ independently of one another are methyl, methoxy or chlorine, $R_{12}$ and $R_{13}$ independently of one another are methyl or hydrogen, X is linear or branched $C_1$–$C_{12}$alkylene, $C_4$–$C_{18}$alkylene which is interrupted one or more times by —O—, or $C_3$–$C_6$alkylene which is substituted by one or two groups of the formula G, or X is a group —CH$_2$—CH=CH—CH$_2$— or is phenylene which is unsubstituted or is substituted by one or two groups of the formula G, or X is a group

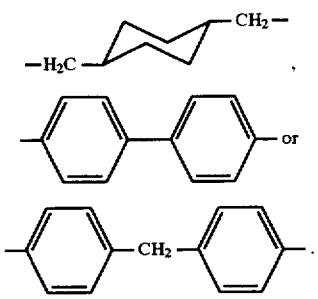

Compounds of the formula I which are of interest are those in which $R_{12}$ is hydrogen, and X is linear or branched $C_1$–$C_{12}$alkylene, $C_4$–$C_{18}$alkylene which is interrupted one or more times by —O—, or $C_3$–$C_6$alkylene which is substituted by one or two groups of the formula G, or X is a group —CH$_2$—CH=CH—CH$_2$—, phenylene or xylylene, or X is a group

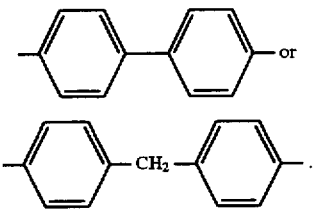

Further preference is given to those compounds of the formula I in which

X is linear or branched $C_1$–$C_{12}$alkylene or $C_4$–$C_{18}$alkylene which is interrupted one or more times by —O—, or X is a group —CH$_2$—CH=CH—CH$_2$—, phenylene, xylylene or

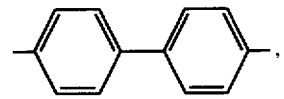

or X is

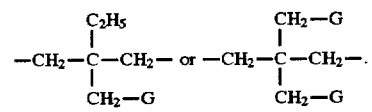

Particular interest attaches to compounds of the formula I in which

Z is oxygen, n and m are 1, $R_1$, $R_2$, $R_3$ and $R_4$ are identical and are phenyl which is substituted two or three times by methyl, chlorine or methoxy, and X is $C_4$–$C_{12}$alkylene,

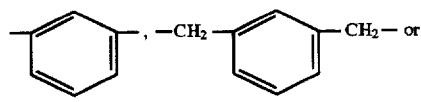

$$-CH_2-\!\!\!\!\!\bigcirc\!\!\!\!\!-CH_2-$$

Particularly preferred compounds of the formula I are those in which $R_1$, $R_2$, $R_3$ and $R_4$ are identical.

Further preferred compounds of the formula I are those in which

Z is oxygen and n and m are 1.

Particular interest is attached, in addition, to compounds of the formula I in which n and m are 1.

Examples of compounds according to the invention are:

1,10-bis[bis(2,6-dimethoxybenzoyl)phosphine oxide] decane,
1,10-bis[bis(2,4,6-trimethylbenzoyl)phosphine oxide] decane,
1,6-bis[bis(2,6-dimethoxybenzoyl)phosphine oxide]hexane,
1,2-bis[bis(2,4,6-trimethylbenzoyl)phosphine oxide]ethane,
1,4-bis[bis(2,6-dichlorobenzoyl)phosphine oxide]decane,
α,ω-bis[bis(2,4,6-trimethylbenzoyl)phosphine oxide]-p-xylylene,
1-[bis(2,6-dimethoxybenzoyl)phosphine oxide]-8-[bis(2,4,6-trimethylbenzoyl)phosphine oxide]3,6-dioxaoctane,
1,1-bis[bis(2,4,6-trimethylbenzoyl)phosphine oxide]1-undecylmethane,
1,6-bis[bis(2-methylnaphth-1-oyl)phosphine oxide]hexane,
1,4-bis[bis(t-butanoyl)phosphine oxide]butane,
1,10-bis[bis(2,4,6-trimethylbenzoyl)phosphine sulfide] decane.

The compounds of the formula I according to the invention can be prepared, for example, by double acylation of a phosphine (1) with at least 4 equivalents of an acid chloride (2) in the presence of at least 4 equivalents of a base, followed by oxidation of the dimeric phosphine (3) obtained to give the corresponding phosphine oxide of the formula (I), or by reaction of the dimeric phosphine (3) with sulfur to give the corresponding phosphine sulfide of the formula (I), in accordance with the scheme:

$$H_2P-X-PH_2 + 4Cl-CO-R \longrightarrow (R-CO)_{\overline{2}}P-X-P(-CO-R)_2$$
$$(1) \quad\quad\quad (2) \quad\quad\quad\quad\quad (3)$$

$$(3) \begin{cases} \xrightarrow{[O]} (R-CO-)_2P-X-P(-CO-R)_2 \overset{O}{\underset{\|}{}}\overset{O}{\underset{\|}{}} \quad (I) \\ \xrightarrow{S_8} (R-CO-)_2P-X-P(-CO-R)_2 \overset{S}{\underset{\|}{}}\overset{S}{\underset{\|}{}} \quad (I) \end{cases}$$

R is as defined above for $R_1$, $R_2$, $R_3$ and $R_4$. X is as defined above.

The asymmetric compounds of the formula (I) are obtained, for example, by using mixtures of acid chlorides (2) where R is different.

Examples of suitable bases are tertiary amines, pyridine, alkali metals, lithium diisopropylamide, butyllithium, alkaline earth metal carbonates, alkali metal alcoholates or alkali metal hydrides. The first step of the reaction is preferably carried out in solution. Suitable solvents are in particular hydrocarbons, such as alkanes and mixtures of alkanes, cyclohexane, benzene, toluene or xylene. Depending on the solvent and the starting materials used, the reaction is carried out at different temperatures. When using bases such as lithium diisopropylamide or butyllithium, for example, it is advantageously carried out at −40°–0° C. The reactions with tertiary amines, alkali metals or alkali metal hydrides as bases, for example, are advantageously carried out at 10°–120° C., preferably 20°–80° C. After the base chloride which has formed has been separated off, the phosphine (3) can be isolated by evaporative concentration. The crude reaction product can be used further without purification or else can be purified, for example by distillation or crystallization. The second step of the reaction, however, can also be carried out without isolation of (3) using the solution of the crude product.

Suitable oxidizing agents for the second step of the preparation of the oxides are in particular hydrogen peroxide and organic peroxy compounds, for example peracetic acid, or air.

The sulfide can be prepared, for example, in analogy to the method described in DE-A-3 034 697. The reaction is advantageously carried out under an inert gas atmosphere comprising, for example, nitrogen, argon or carbon dioxide, preferably nitrogen. Following the reaction it may be necessary to carry out filtration in order to separate the sulfide formed or its solution from any sulfur which may still be present. The reaction products can be purified by conventional methods, for example by crystallization or chromatography.

The primary phosphines (1) which are used as starting material are known compounds, some of which are commercially available, or can be prepared in analogy to known compounds. The preparation is described, for example, by G. Kosolapoff and L. Maier in Organic Phosphorous Compounds, Vol. I, Wiley Interscience, 1972.

Thus the phosphines (1) can be prepared, for example, by reacting the dibromide (4) with a phosphite (5) or with the sodium salt of a phosphonate (6) to give the corresponding dimeric ester (7) which can be reacted by reduction, for example using lithium aluminium hydride, to give the phosphine (1).

$$Br-X-Br \begin{cases} \xrightarrow{P(OR')_3 \ (5)} \\ \xrightarrow{NaOP(OR')_2 \ (6)} \end{cases} (R'O)_2P-X-P(OR')_2 \overset{O}{\underset{\|}{}}\overset{O}{\underset{\|}{}}$$
$$(4) \quad\quad\quad\quad\quad\quad\quad\quad\quad (7)$$

$$(7) \xrightarrow{LiAlH_4} H_2P-X-PH_2$$
$$\quad\quad\quad\quad (1)$$

R' is for example $C_1$–$C_4$alkyl.

The reactions are carried out under conditions which are known to those skilled in the art. Such reactions are described, for example, in Inorg. Synth. 14 (1973), page 10. The hydrogenation using $LiAlH_4$ [(7)→(1)] can also be found, for example, in Helv. Chim. Acta 1966, No. 96, page 842.

The acid chlorides of the formula (2) are prepared by known methods from the prior art.

The compounds according to the invention are photoinitiators of low volatility which have good solution properties in the substrates to be polymerized.

In accordance with the invention, the compounds of the formula I can be used as photoinitiators for the photopolymerization of ethylenically unsaturated compounds or of mixtures which contain such compounds. This use may also be practiced in combination with another photoinitiator and/or with other additives.

The invention therefore also relates to photopolymerizable compositions comprising
  (a) at least one ethylenically unsaturated photopolymerizable compound, and
  (b) as photoinitiator, at least one compound of the formula I it being possible for the composition to contain other photoinitiators and/or other additives in addition to component (b).

The unsaturated compounds may contain one or more olefinic double bonds. They may be of low molecular weight (monomeric) or of relatively high molecular weight (oligomeric). Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also of interest. Further examples are acrylonitrile, acrylamide, methacrylamide, N-substituted (meth)acrylamides, vinyl esters such as vinyl acetate, vinyl ethers such as isobutyl vinyl ether, styrene, alkylstyrenes and halostyrenes, N-vinylpyrrolidone, vinyl chloride or vinylidene chloride.

Examples of monomers containing two or more double bonds are the diacrylates of ethylene glycol, propylene glycol, neopentylglycol, hexamethylene glycol or bisphenol A, and also 4,4'-bis(2-acryloyloxyethoxy)diphenylpropane, trimethylolpropane triacrylate, pentaerythritol triacrylate or pentaerythritol tetraacrylate, vinyl acrylate, divinylbenzene, divinyl succinate, diallyl phthalate, triallyl phosphate, triallyl isocyanurate or tris(2-acryloylethyl)isocyanurate.

Examples of relatively high molecular weight (oligomeric) polyunsaturated compounds are acrylicized epoxy resins, and polyesters, polyurethanes and polyethers which are acrylicized or contain vinyl ether or epoxy groups. Further examples of unsaturated oligomers are unsaturated polyester resins which are mostly prepared from maleic acid, phthalic acid and one or more diols and have molecular weights of from about 500 to 3000. In addition it is also possible to employ vinyl ether monomers and vinyl ether oligomers, and also maleate-terminated oligomers having polyester, polyurethane, polyether, polyvinyl ether and epoxy main chains. Combinations of vinyl ether group-containing oligomers and polymers as are described in WO 90/01512 are particularly highly suitable. However, copolymers of vinyl ether and maleic acid-functionalized monomers are also appropriate. Such unsaturated oligomers can also be referred to as prepolymers.

Examples of particularly suitable compounds are esters of ethylenically unsaturated carboxylic acids and polyols or polyepoxides, and polymers containing ethylenically unsaturated groups in the chain or in the side groups, for example unsaturated polyesters, polyamides and polyurethanes and copolymers thereof, polybutadiene and butadiene copolymers, polyisoprene and isoprene copolymers, polymers and copolymers containing (meth)acrylic groups in the side chains, and mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic acid and methacrylic acid are preferred.

Suitable polyols are aromatic and, in particular, aliphatic and cycloaliphatic polyols. Examples of aromatic polyols are hydroquinone, 4,4'-dihydroxybiphenyl, 2,2-di(4-hydroxyphenyl)propane, and also novolaks and resols. Examples of polyepoxides are those based on said polyols, especially aromatic polyols and epichlorohydrin. Other suitable polyols include polymers and copolymers which contain hydroxyl groups in the polymer chain or in side groups, for example polyvinyl alcohol and copolymers thereof or hydroxyalkyl polymethacrylates or copolymers thereof. Other suitable polyols are oligoesters containing hydroxyl end groups.

Examples of aliphatic and cycloaliphatic polyols are alkylenediols, preferably having 2 to 12 carbon atoms, such as ethylene glycol, 1,2- or 1,3-propanediol, 1,2-, 1,3- or 1,4-butanediol, pentanediol, hexanediol, octanediol, 1,4-butanediol, pentanediol, hexanediol, octanediol, dodecanediol, diethylene glycol, triethylene glycol, polyethylene glycol having molecular weights of preferably from 200 to 1500, 1,3-cyclopentanediol, 1,2-, 1,3- or 1,4-cyclohexanediol, 1,4-dihydroxymethylcyclohexane, glycerol, tris-(β-hydroxyethyl)amine, trimethylolethane, trimethylolpropane, pentaerythritol, dipentaerythritol and sorbitol.

The polyols may be partially or fully esterified by means of one or more unsaturated carboxylic acids, where the free hydroxyl groups in partial esters may be modified, for example etherified or esterified with other carboxylic acids.

Examples of esters are:

trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritoldimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitolhexaacrylate, oligoester acrylates and methacrylates, glycerol di- and triacrylate, 1,4-cyclohexane diacrylate, bisacrylates and bismethacrylates of polyethylene glycol having molecular weights of from 200 to 1500, or mixtures thereof.

Further suitable components (a) are the amides of identical or different unsaturated carboxylic acids of aromatic, cycloaliphatic and aliphatic polyamines, preferably having 2 to 6, in particular 2 to 4, amino groups. Examples of polyamines of this type are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy) or di(β-aminopropoxy)ethane. Other suitable polyamines are polymers and copolymers which may contain additional amino groups in the side chain, and oligoamides containing amino end groups. Examples of unsaturated amides of this type are: methylenebisacrylamide, 1,6-hexamethylenebisacrylamide, diethylenetriaminetrismethacrylamide, bis(methacrylamidopropoxy)ethane, β-methacrylamidoethyl methacrylate, and N-[(β-hydroxyethoxy)ethyl]acrylamide.

Suitable unsaturated polyesters and polyamides are derived, for example, from maleic acid and diols or diamines. Some of the maleic acid may be replaced by other dicarboxylic acids. They can be employed together with ethylenically unsaturated comonomers, for example styrene. The polyesters and polyamides may also be derived from dicarboxylic acids and ethylenically unsaturated diols or diamines, in particular from relatively long chain compounds containing, for example, 6 to 20 carbon atoms. Examples of polyurethanes are those built up from saturated or unsaturated diisocyanates and from unsaturated or saturated diols.

Polybutadiene and polyisoprene and copolymers thereof are known. Examples of suitable comonomers are olefins such as ethylene, propene, butene, hexene, (meth)acrylate, acrylonitrile, styrene and vinyl chloride. Polymers containing (meth)acrylate groups in the side chain are also known. These may be, for example, products of the reaction of novolak-based epoxy resins with (meth)acrylic acid, homopolymers or copolymers of vinyl alcohol or hydroxyalkyl derivatives thereof which have been esterified using (meth)acrylic acid, or homopolymers and copolymers of (meth)acrylates which have been esterified using hydroxyalkyl (meth)acrylates.

The photopolymerizable compounds may be employed alone or in any desired mixtures. Preference is given to mixtures of polyol (meth)acrylates. It is also possible to add binders to the compositions according to the invention; this is particularly expedient if the photopolymerizable compounds are liquid or viscous substances. The quantity of binder may be for example, 5–95% by weight, preferably 10–90% by weight and, in particular, 40–90% by weight, based on the overall solids content. The binder is chosen depending on the field of application and on the properties required therefor, such as the facility for development in aqueous and organic solvent systems, adhesion to substrates and sensitivity to oxygen.

Examples of suitable binders are polymers having a molecular weight of about 5000–2,000,000, preferably 10,000–1,000,000. Examples are homo- and copolymeric acrylates and methacrylates, for example copolymers of methyl methacrylate/ethyl acrylate/methacrylic acid, poly (alkyl methacrylates), poly(alkyl acrylates); cellulose esters and cellulose ethers, such as cellulose acetate, cellulose acetate butyrate, methylcellulose and ethylcellulose; polyvinylbutyral, polyvinylformal, cyclized rubber, polyethers, such as polyethylene oxide, polypropylene oxide and polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly (ethylene/vinyl acetate), polymers such as polycaprolactam and poly(hexamethyleneadipamide), and polyesters such as poly(ethylene glycol terephthalate) and poly(hexamethylene glycol succinate).

The unsaturated compounds may also be used in mixtures with non-photopolymerizable film-forming components. These may be, for example, physically drying polymers or solutions thereof in organic solvents, for example nitrocellulose or cellulose acetobutyrate. However, they may also be chemically curable or heat-curable resins such as, for example, polyisocyanates, polyepoxides or melamine resins. The additional use of heat-curable resins is important for use in so-called hybrid systems, which are photopolymerized in a first step and crosslinked by thermal aftertreatment in a second step.

The photopolymerizable mixtures may contain various additives in addition to the photoinitiator. Examples thereof are thermal inhibitors, which are intended to prevent premature polymerization, for example the hydroquinone, hydroquinine derivatives, p-methoxyphenol, β-naphthol or sterically hindered phenols such as 2,6-di(tert-butyl)-p-cresol. The shelf life in the dark can be increased, for example, by using copper compounds such as copper naphthenate, copper stearate or copper octanoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. In order to exclude atmospheric oxygen during the polymerization, paraffin or similar wax-like substances can be added; these migrate to the surface on commencement of the polymerization because of their low solubility in the polymer, and form a transparent surface layer which prevents the ingress of air. Light stabilizers which can be added in small quantities are UV absorbers, for example those of the hydroxyphenylbenzotriazole, hydroxyphenylbenzophenone, oxalamide or hydroxyphenyl-s-triazine type. These compounds can be employed individually or as mixtures, with or without the use of sterically hindered amines (HALS).

Examples of such UV absorbers and light stabilizers are:

1. 2-(2'-Hydroxyphenyl)benzotriazoles, for example 2-(2'-hydroxy-5'-methylphenyl) benzotriazole, 2-(3',5'-di-tert-butyl-2'-hydroxyphenyl) benzotriazole, 2-(5'-tert-butyl-2'-hydroxyphenyl) benzotriazole, 2-(2'-hydroxy-5'-(1,1,3,3-tertamethylbutyl)phenyl)benzotriazole, 2-(3',5'-di-tertbutyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3-tert-butyl-5'-[2-(2-ethylhexyloxy)carbonylethyl]-2'-hydroxyphenyl)-5-chlorobenzotriazole, 2-(3'-tertbutyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-yl phenol]; transesterification product of 2-[3'-tert-butyl-5'-(2-methoxycarbonylethyl)-2'-hydroxyphenyl] benzotriazole with polyethylene glycol 300; [R—CH$_2$CH$_2$—COO(CH$_2$)$_3$H$_2$— where R=3'-tertbutyl-4'-hydroxy-5'-2H-benzotriazol-2-yl phenyl.

2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

3. Esters of unsubstituted or substituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl and isooctyl α-cyano-β,β-diphenylacrylate, methyl α-carbomethoxycinnamate, methyl and butyl α-cyano-β-methyl-p-methoxycinnamate, methyl α-carbomethoxy-p-methoxycinnamate and N-(β-carbomethoxy-β-cyanovinyl)-2-methylindoline.

5. Sterically hindered amines, for example bis(2,2,6,6-tetramethylpiperidyl)sebacate, bis(2,2,6,6-tetramethylpiperidyl)succinate, bis(1,2,2,6,6-pentamethylpiperidyl)sebacate, bis(1,2,2,6,6-pentamethylpiperidyl)n-butyl-3,5-di-tert-butyl-4-hydroxybenzylmalonate, the product of the condensation of 1-hydroxyethyl-2,2,6,6-tetramethyl-4-hydroxypiperidine and succinic acid, the product of the condensation of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetrate, tetrakis(2,2,6,6-tetramethyl-4-piperidyl)1,2,3,4-butanetetraoate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, the product of the condensation of N,N'-bis(2,2,6,6-tetramethyl-4-piperidyl)hexamethylene diamine and 4-morpholino-2,6-dichloro-1,3,5-triazine, the product of the condensation of 2-chloro-4,6-di(4-n-butylamino-2,2,6,6-tetramethylpiperidyl)1,3,5-triazine and 1,2-bis(3-aminopropylamino)ethane, the product of the condensation of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and mixtures thereof with 2-ethoxy-2'-ethyl-5,4'-di-tert-butyloxanilide, and mixtures of o- and p-methoxy- and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butoxypropoxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine and 2-[4-dodecyl/tridecyloxy(2-hydroxypropyl)oxy-2-hydroxyphenyl]-4,6-bis(2,4-dimethylphenyl)-1,3,5-triazine.

8. Phosphites and phosphonites, for example triphenyl phosphite, diphenyl alkyl phosphite, phenyl dialkylphosphite, tris-(nonylphenyl) phosphite, trilauryl phosphite, trioctadecyl phosphite, distearyl pentaerythrityl diphosphite, tris(2,4-di-tert-butylphenyl)phosphite, diisodecylpentaerythrityl diphosphite, bis(2,4-di-tert-butylphenyl)pentaerythrityl diphosphite, bis(2,6-di-tert-butyl-4-methylphenyl) pentaerythrityl diphosphite, bisisodecyloxy-pentaerythrityl diphosphite, bis(2,4-di-tert-butyl-6-methylphenyl)pentaerythrityl diphosphite, bis(2,4,6-tri-tert-butylphenyl)pentaerythrityl diphosphite, tristearylsorbitoltriphosphite, tetrakis-(2,4-di-tert-butylphenyl)-4,4'-biphenylenediphosphonite, 6-isooctyloxy-2,4,8,10-tetra-tert-butyl-12H-dibenz[d,g]-1,3,2-dioxaphosphocine, 6-fluoro-2,4,8,10-tetra-tert-butyl-12-methyl-dibenz[d,g]-1,3,2-dioxaphosphocine, bis(2,4-di-tert-butyl-6-methylphenyl)methyl phosphite, and bis(2,4-di-tert-butyl-6-methylphenyl)ethyl phosphite.

The invention also relates to compositions to which, as additional additive, a UV absorber from the class of hydroxyphenylbenzotriazole, hydroxyphenylbenzophenone, oxalamide or hydroxyphenyl-s-triazine compounds is added, if desired in the presence of a sterically hindered mine.

Such compositions according to the invention are preferably used for the preparation of UV-curable powder coatings.

To accelerate the photopolymerization it is possible to add amines such as, for example, triethanolamine, N-methyldiethanolamine, ethyl p-dimethylaminobenzoate or Michlers ketone. The action of the amines can be intensified by the addition of aromatic ketones of the benzophenone type. Examples of amines which can be used as oxygen scavengers are substituted N,N-dialkylanilines as described in EP-A-339 841. The photopolymerization can also be accelerated by addition of photosensitizers which shift or broaden the spectral sensitivity. These are, in particular, aromatic carbonyl compounds such as benzophenone derivatives, thioxanthone derivatives, anthraquinone derivatives and 3-acylcoumarin derivatives and 3-(arylmethylene) thiazolines, and also eosin, rhodanine and erythrosine dyes. The curing process may be assisted, in particular, by compositions pigmented with $TiO_2$, for example, but also by addition of a component which forms free radicals under thermal conditions, for example an azo compound such as 2,2'-azobis(4-methoxy-2,4-dimethylvaleronitrile) or a peroxy compound such as a hydroperoxide or peroxycarbonate, for example t-butyl hydroperoxide, as described in EP-A 245 639, for example.

The compositions according to the invention may also contain a photoreducible dye, for example a xanthene, benzoxanthene, benzothioxanthene, thiazine, pyronine, porphyrin or acridine dyes, and/or a trihalomethyl compound which can be cleaved by radiation. Similar compositions are described in, for example, EP-A-445 624.

Other conventional additives are—depending on the application—optical brighteners, fillers, pigments, dyes, wetting agents or levelling assistants. Thick and pigmented coatings can suitably be cured by the addition of glass microbeads or powdered glass fibres, as described in U.S. Pat. No. 5,013,768, for example.

The invention also relates to compositions comprising as component (a) at least one ethylenically unsaturated, photopolymerizable compound which is emulsified or dissolved in water.

Radiation-curable, aqueous prepolymer dispersions of this type are commercially available in many variations. This term is taken to mean a dispersion of water and at least one prepolymer dispersed therein. The concentration of the water in these systems is, for example, from 5 to 80% by weight, in particular from 30 to 60% by weight. The radiation-curable prepolymer or prepolymer mixture is present, for example, in concentrations of from 95 to 20% by weight, in particular from 70 to 40% by weight. The total of the percentages indicated for water and prepolymer in these compositions is in each case 100, to which are added the assistants and additives in various amounts depending on the application.

The radiation-curable, water-dispersed, film-forming prepolymers, which are frequently also dissolved, are, for aqueous prepolymer dispersions, monofunctional or polyfunctional ethylenically unsaturated prepolymers which are known per se, can be initiated by means of free radicals and contain, for example, from 0.01 to 1.0 mol of polymerizable double bonds per 100 g of prepolymer, and have an average molecular weight of, for example, at least 400, in particular from 500 to 10,000. Depending on the intended application, however, prepolymers having higher molecular weights may also be suitable. For example, polyesters containing polymerizable C—C double bonds and having a maximum acid number of 10, polyethers containing polymerizable C—C double bonds, hydroxyl-containing products of the reaction of a polyepoxide containing at least two epoxide groups per molecule with at least one α,β-ethylenically unsaturated carboxylic acid, polyurethane (meth)acrylates and α,β-ethylenically unsaturated acrylic copolymers containing acrylic radicals, as described in EP-A-12 339, are used. Mixtures of these prepolymers may also be used. Also suitable are the polymerizable prepolymers described in EP-A-33 896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions based on specific alkyl(meth)acrylate polymers are described in EP-A-41 125, and suitable water-dispersible, radiation-curable prepolymers made from urethane acrylates are disclosed in DE-A-2 936 039.

These radiation-curable, aqueous prepolymer dispersions may contain, as further additives, dispersion assistants, emulsifiers, antioxidants, light stabilizers, dyes, pigments, fillers, for example talc, gypsum, silica, rutile, carbon black, zinc oxide and iron oxides, reaction accelerators, levelling agents, lubricants, wetting agents, thickeners, matting agents, antifoams and other assistants which are conventional in surface-coating technology. Suitable dispersion assistants are water-soluble, high molecular weight organic compounds containing polar groups, for example polyvinyl alcohols, polyvinylpyrrolidone and cellulose ethers. Emulsifiers which can be used are nonionic emulsifiers and possibly also ionic emulsifiers.

The photopolymerizable compositions contain the photoinitiator (b) advantageously in a quantity of from 0.05 to 15% by weight, preferably from 0.1 to 5% by weight, based on the composition.

In certain cases it may be of advantage to use mixtures of two or more of the photoinitiators according to the invention. It is of course also possible to use mixtures with known photoinitiators, for example mixtures with benzophenone, acetophenone derivatives, for example α-hydroxycycloalkylphenyl ketones, dialkoxyacetophenones, α-hydroxy- or α-aminoacetophenones, 4-aroyl-1,3-dioxolanes, benzoin alkyl ethers and benzil ketals, monoacylphosphine oxides, bisacylphosphine oxides or titanocenes. When the photoinitiators according to the invention are employed in hybrid systems, cationic photoinitiators such as aromatic sulfonium or iodonium salts or cyclopentadienylareneiron(II) complex salts are used in addition to the free-radical curing agents according to the invention.

The invention also relates to compositions in which the additional photoinitiators are compounds of the formula (XV)

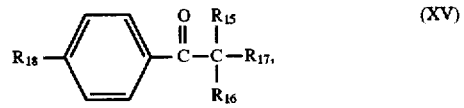

in which $R_{18}$ is hydrogen, $C_1$–$C_{18}$alkyl, $C_1$–$C_{18}$alkoxy, —OCH$_2$CH$_2$—OR$_{19}$, a group

or a group

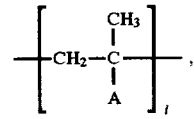

in which l has a value from 2 to 10 and

A is the radical

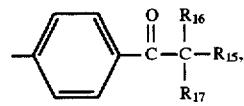

$R_{15}$ and $R_{16}$ independently of one another are hydrogen, $C_1$–$C_6$alkyl, phenyl, $C_1$–$C_{16}$alkoxy or —O(CH$_2$CH$_2$O)$_q$—$C_1$–$C_{16}$alkyl in which q is a number from 1–20, or $R_{15}$ and $R_{16}$, together with the carbon atom to which they are attached, form a cyclohexyl ring, $R_{17}$ is hydroxyl, $C_1$–$C_{16}$alkoxy or —O(CH$_2$CH$_2$O)$_q$—$C_1$–$C_{16}$alkyl, $R_{15}$, $R_{16}$ and $R_{17}$ not all simultaneously being $C_1$–$C_{16}$alkoxy or —O(CH$_2$CH$_2$O)$_q$—$C_1$–$C_{16}$alkyl, and $R_{19}$ is hydrogen,

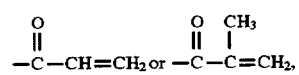

and/or the additional photoinitiators are of the formula (XVI)

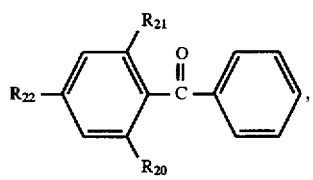

in which $R_{20}$, $R_{21}$ and $R_{22}$ independently of one another are hydrogen or methyl, or the additional photoinitiators are mixtures of compounds of the formulae (XV) and (XVI).

$C_1$–$C_{18}$Alkyl $R_{18}$, $C_1$–$C_6$alkyl, $R_{15}$ and $R_{16}$ and $C_1$–$C_4$alkyl $R_{17}$ may be as defined for $R^1$ except for the respective number of carbon atoms.

$C_1$–$C_{18}$Alkoxy $R_{18}$ is, for example, branched or unbranched alkoxy such as methyloxy, ethyloxy, n-propyloxy, isopropyloxy, n-butyloxy, isobutyloxy, sec-butyloxy, tert-butyloxy, pentyloxy, hexyloxy, heptyloxy, octyloxy, 2,4,4-trimethylpent-1-yloxy, 2-ethylhexyloxy, nonyloxy, decyloxy, dodecyloxy or octadecyloxy.

$C_1$–$C_6$Alkoxy $R_{15}$, $R_{16}$ and $R_{17}$ may be as defined for $R_{18}$ except for the appropriate number of carbon atoms; they are preferably decyloxy, methoxy or ethoxy, especially methoxy or ethoxy.

The radical —O(CH$_2$CH$_2$O)$_q$—C$_1$–C$_{16}$alkyl represents 1 to 20 successive ethylene oxide units whose chain is terminated by a $C_1$–$C_{16}$alkyl radical.

q is preferably from 1 to 10, for example 1 to 8, in particular 1 to 6. The ethylene oxide unit chain is preferably terminated by a $C_1$–$C_{10}$alkyl radical, for example a $C_1$–$C_8$alkyl radical, in particular a $C_1$–$C_4$alkyl radical.

Preference is given to compositions in which $R_{15}$ and $R_{16}$ in the formula (XV) are independently of one another $C_1$–$C_6$alkyl or, together with the carbon atoms to which they are attached, form a cyclohexyl ring, and $R_{17}$ is hydroxyl.

Further preferred compositions are those in which the proportion of compounds of the formula (I) in the mixture with compounds of the formulae (XV) and/or (XVI) is from 5 to 95%, preferably from 5 to 50%.

Other important compositions are those in which $R_{15}$ and $R_{16}$ in the compounds of the formula (XV) are identical and are methyl, and $R_{17}$ is hydroxyl or isopropoxy.

Preference is likewise given to compositions comprising compounds of the formula (I) and a mixture of compounds of the formula (XVI) in which compounds of the formula (XVI) where $R_{20}$ and $R_{22}$ are hydrogen and $R_{21}$ is methyl are present to the extent of 20% and compounds of the formula (XVI) where $R_{20}$, $R_{21}$ and $R_{22}$ are methyl are present to the extent of 80%.

Compositions of prime interest are those as described above which contain photoinitiator mixtures of the formulae (I), (XV) and/or (XVI) and which are liquid at room temperature.

The preparation of the compounds of the formulae (XV) and (XVI) is known in general terms, and some of the compounds are commercially available. The preparation of oligomeric compounds of the formula (XV) is described, for example, in EP-A-0 161 463. A description of the preparation of compounds of the formula (XVI) is given, for example, in EP-A-209 831.

The photopolymerizable compositions can be used for various purposes, for example as printing inks, as varnishes or clearcoats, as white paints, for example for wood or metal, as coating compositions, inter alia, for paper, wood, metal or plastic, as powder coatings, as daylight-curable coatings for buildings and roadmarking, for photographic reproduction processes, for holographic recording materials, for image recording processes or for the production of printing plates which can be developed using organic solvents or aqueous-alkaline media, for the production of masks for screen printing, as dental filling materials, as adhesives, as pressure-sensitive adhesives, as laminating resins, as etch resists or permanent resists and as solder masks for electronic circuits, for the production of three-dimensional articles by bulk curing (UV curing in transparent moulds) or by the stereolithography process, as described, for example, in U.S. Pat. No. 4,575,330, for the preparation of composite materials (for example styrenic polyesters, which may contain glass fibres and other assistants) and other thick-layer compositions, for the coating or encapsulation of electronic components or as coatings for optical fibres. The compounds according to the invention may also be used as initiators for emulsion polymerizations, as initiators of a polymerization for the fixing of ordered states of liquid-crystalline mono- and oligomers, as initiators for the fixing of dyes to organic materials, and for curing powder coatings.

In surface coatings, mixtures of a prepolymer with polyunsaturated monomers are often used which also contain a monounsaturated monomer. The prepolymer here is primarily responsible for the properties of the coating film, and variation thereof allows the person skilled in the art to influence the properties of the cured film. The polyunsaturated monomer functions as a crosslinking agent which renders the coating film insoluble. The monounsaturated monomer functions as a reactive diluent by means of which the viscosity is reduced without the need to use a solvent.

Unsaturated polyester resins are mostly used in two-component systems in conjunction with a monounsaturated monomer, preferably styrene. For photoresists, specific one-component systems are frequently employed, for example polymaleimides, polychalcones or polyimides, as described in DE-A 2 308 830.

The compounds according to the invention and mixtures thereof may also be used as free-radical photoinitiators or photoinitiating systems for radiation-curable powder coatings. The powder coatings may be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (e.g. methyl methacrylamidoglycolate) and with a free-radical photoinitiator according to the invention, as described, for example, in the paper "Radiation Curing of Powder Coating", Conference Proceedings, Radtech Europe 1993 by M. Wittig and Th. Gohmann. Similarly, free-radically UV-curable powder coatings can be formulated by mixing unsaturated polyester resins with solid acrylates, methacrylates or vinyl ethers and with a photoinitiator (or mixture of photoinitiators) according to the invention. The UV-curable powder coatings may also comprise white or coloured pigments. Thus, for example, preferably rutile titanium dioxide can be employed in concentrations of up to 50% by weight in order to give a cured powder coating having good covering power. The process normally comprises electrostatic or tribostatic spraying of the powder onto the substrate, for example of metal or wood, melting the powder by heating and, after a smooth film has been formed, radiation-curing of the coating using ultraviolet and/or visible light, for example with medium-pressure mercury lamps, metal halide lamps or xenon lamps. A particular advantage of the radiation-curable powder coatings over their heat-curable counterparts is that the flow time after the melting of the powder particles can be selectively extended in order to ensure the formation of a smooth, high-gloss coating. In contrast to heat-curable systems, radiation-curable powder coatings can be formulated without the unwanted effects of a reduction in their lifetime so that they melt at relatively low temperatures. For this reason, they are also suitable as coatings for heat-sensitive substrates such as wood or plastics.

In addition to the photoinitiators according to the invention, the powder coating formulations may also contain UV absorbers. Appropriate examples have been listed above unders items 1–8.

The photocurable compositions according to the invention are suitable, for example, as coating substances for substrates of all kinds, for example wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$, on which it is desired to apply a protective coating or, by imagewise exposure, an image.

The substrates can be coated by applying a liquid composition, a solution or suspension to the substrate. The choice of the solvent and the concentration depend predominantly on the type of composition and the coating procedure. The solvent should be inert: in other words it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. Using known coating processes, the solution is applied evenly to a substrate, for example by spincoating, dip coating, knife coating, curtain coating, brushing, spraying—especially electrostatic spraying—and reverse roll coating. It is also possible to apply the photosensitive layer to a temporary, flexible support and then to coat the final substrate, for example a copper-laminated circuit board, by means of layer transfer via lamination.

The quantity applied (layer thickness) and the nature of the substrate (layer support) are functions of the desired application. The range of coat thicknesses generally comprises values from about 0.1 µm to more than 10 µm.

The radiation-sensitive compositions according to the invention find application as negative resists which have a very high photosensitivity and can be developed in an aqueous-alkaline medium without swelling. They are suitable as photoresists for electronic (galvanoresists, etch resists and solder resists), the production of printing plates such as offset printing plates or screen printing formes, and can be used for chemical milling or as microresists in the production of integrated circuits. There is a correspondingly wide range of variation in the possible layer supports and the processing conditions for the coated substrates.

Examples of the layer supports for photographic information recording are films made of polyester, cellulose acetate or plastic-coated paper, for offset printing plates, specially treated aluminium; for the production of printed circuits, copper-faced laminates; and for the production of integrated circuits, silicon wafers. The layer thicknesses for photographic materials and offset printing plates are generally from about 0.5 µm to 10 µm, while for printed circuits they are from 0.4 µm to about 2 µm.

Following the coating of the substrates, the solvent is generally removed by drying to leave a layer of the photoresist on the substrate.

The term "imagewise exposure" relates both to exposure through a photomask containing a predetermined pattern, for example a slide, exposure by a laser beam which is moved under control from a computer, for example, over the surface of the coated substrate, thereby generating an image, and irradiation with computer-controlled electron beams.

Following the imagewise exposure of the material and prior to developing, it may be advantageous to carry out a brief thermal treatment, in which only the exposed parts are thermally cured. The temperatures employed are generally 50°–150° C. and preferably 80°–130° C.; the duration of the thermal treatment is generally between 0.25 and 10 minutes.

The photocurable composition can also be used in a process for the production of printing plates or photoresists as described, for example, in DE-A-4 013 358. In this process the composition is exposed before, simultaneously with or after the imagewise irradiation, exposure being carded out for a short period with visible light at a wavelength of at least 400 nm without a mask.

Following the exposure and the optional thermal treatment, the unexposed areas of the photoresist are removed using a developer in a manner known per se.

As already mentioned, the compositions according to the invention can be developed by aqueous-alkaline media. Suitable aqueous-alkaline developer solutions are, in particular, aqueous solutions of tetraalkylammonium hydroxides or of alkali metal silicates, phosphates, hydroxides and carbonates. Relatively small quantities of wetting agents and/or organic solvents may also be added, if desired, to these solutions. Examples of typical organic solvents which may be added in small quantities to the developing liquids are cyclohexanone, 2-ethoxyethanol, toluene, acetone and mixtures of such solvents.

Photocuring is of considerable importance for printing inks, since the drying time of the binder is a crucial factor for the production rate of graphic products and should be in the order of fractions of seconds. UV-curable inks are important, in particular, for screen printing.

As already mentioned, the mixtures according to the invention are also highly suitable for the production of printing plates, where, for example, mixtures of soluble, linear polyamides or styrene/butadiene or styrene/isoprene rubber, polyacrylates or polymethyl methacrylates containing carboxyl groups, polyvinyl alcohols or urethane acrylates are used with photopolymerizable monomers, for example acrylamides, methacrylamides, acrylates or methacrylates, and a photoinitiator. Films and plates made from these systems (wet or dry) are exposed through the negative (or positive) of the print original, and the uncured parts are subsequently washed out using a suitable solvent.

A further area of application for photocuring is in the coating of metals, for example in the coating of metal sheets and tubes, cans or bottle caps, and the photocuring of plastic coatings, for example PVC-based wall or floor coverings.

Examples of the photocuring of paper coatings are the colourless coating of labels, record sleeves or book covers.

The use of the compounds according to the invention for curing shaped articles made form composite compositions is likewise of interest. The composite composition is made up of a self-supporting matrix material, for example a glass-fibre fabric, which is impregnated with the photocuring formulation. Shaped articles which are produced from composite compositions, using the compounds according to the invention, are of high mechanical stability and resistance.

The compounds according to the invention can also be employed as photocuring agents in moulding, impregnating and coating compositions, as described, for example, in EP-A-7086. Examples of such compositions are fine coating resins on which stringent requirements are placed with respect to their curing activity and yellowing resistance, or fibre-reinforced mouldings such as planar or longitudinally or transversely corrugated light diffusing panels. Processes for the production of such mouldings, for example hand lay-up, spray lay-up, centrifugal or filament winding processes, are described by, for example P. H. Selden in "Glasfaserverstärkte Kunststoffe"[Glass fibre-reinforced plastics], page 610, Springer Verlag Berlin-Heidelberg-New York 1967. Examples of articles which can be produced by this process are boats, chipboard or plywood panels coated on both sides with glass fibre-reinforced plastic, pipes, containers and the like. Other examples of moulding, impregnating and coating compositions are UP resin fine coatings for mouldings containing glass fibres (GRP), e.g. corrugated sheets and paper laminates. Paper laminates may also be based on urea or melamine resins. The fine coating is produced on a support (for example a film) prior to the production of the laminate. The photocurable compositions according to the invention can also be used for casting resins or for encapsulating articles such as electronic components and the like. Curing employs medium-pressure mercury lamps as are conventional in UV curing. However, less intense lamps are also of particular interest, for example those of the type TL40W/03 or TL40W/05. The intensity of these lamps corresponds approximately to that of sunlight. Direct sunlight can also be used for curing. A further advantage is that the composite composition can be removed from the light source in a partially cured, plastic state and can be deformed. Curing is subsequently carried out to completion.

Also important is the use of photocurable compositions for imaging processes and for the optical production of information carriers. In these applications, the coat (wet or dry) applied to the support is irradiated—as already described above—with UV or visible light through a photomask and the unexposed areas of the coat are removed by treatment with a solvent (=developer). The photocurable layer can also be applied by electrodeposition to metal. The exposed areas are crosslinked/polymeric and thus insoluble and remain on the support. If appropriate colouration is carried out, visible images are formed. If the support is a metallized layer, then the metal can be removed from the unexposed areas by etching after exposure and development or can be increased in thickness by electroplating. In this way, printed electronic circuits and photoresists can be produced.

The photosensitivity of the compositions according to the invention generally ranges from the UV region (about 200 nm) up to about 600 nm, and therefore spans a very wide range. Suitable radiation comprises, for example, sunlight or light from artificial sources. Therefore, a large number of very different types of light source can be used. Both point sources and flat radiators (lamp carpets) are appropriate. Examples are carbon arc lamps, xenon arc lamps, medium-pressure, high-pressure and low-pressure mercury lamps, doped with metal halides if desired (metal halogen lamps), microwave-stimulated metal vapour lamps, excimer lamps, superactinic fluorescent tubes, fluorescent lamps, incandescent argon lamps, electronic flashlights, photographic flood lamps, electron beams and X-rays, produced by means of synchrotrons, or laser plasma. The distance between the lamp and the substrate according to the invention which is to be coated can vary depending on the application and on the type and/or power of the lamp, for example from between 2 cm and 150 cm. Of particular suitability are laser light sources, for example excimer lasers, such as krypton F lasers for exposure at 248 nm. Lasers in the visible range may also be employed. In this case the high sensitivity of the materials according to the invention is very advantageous. By this method it is possible to produce printed circuits in the electronics industry, lithographic offset printing plates or relief printing plates, and photographic image recording materials.

The term daylight or daylight-equivalent light sources refers to radiation of wavelength 300–500 nm. In this context, radiation of wavelength 350–450 nm, in particular, must be present for curing. In contrast to the conventional UV curing with high-intensity radiation, in daylight curing the curing effect is achieved by the action of lower-intensity radiation over a longer period. Examples of such radiation are sunlight, and radiation sources which are equivalent to daylight. Sunlight differs from the light from the artificial radiation sources which are usual and customary in UV curing in respect of its spectral composition and intensity. The absorption characteristics and the radical-forming properties of the bisacylphosphine oxides employed in the process according to the invention are particularly suitable for utilizing sunlight as natural radiation source for the curing.

The dimeric bisacylphosphine oxides employed in the process according to the invention give tack-free surfaces within 1–120, for example 1–60, 1–30, in particular 1–15 minutes on irradiation with daylight or with daylight-equivalent light sources. The radiation intensities of the radiation which can be utilized for curing are in the range 10–30 mW/cm$^2$, preferably 10–20 mW/cm$^2$. The intensities of the artificial radiators which are commonly employed in UV curing, on the other hand, are greater than 50 mW/cm$^2$ in the UV region. The term daylight-equivalent artificial light sources, as may be used in the process according to the invention, refers to low-intensity radiators such as, for instance, certain fluorescent lamps, e.g. the TL05 Philips special fluorescent lamp or the TL09 Philips special lamp.

Consequently the invention also relates to the use of compounds of the formula I in which $R_{11}$ and $R_{14}$ are $C_1$–$C_4$alkyl and $R_{12}$ and $R_{13}$ are hydrogen, $C_1$–$C_4$alkyl, $C_1$–$C_4$alkoxy or chlorine for the curing of ethylenically unsaturated compounds using daylight or daylight-equivalent light sources, and to a method of curing ethylenically unsaturated polymerizable compounds, which comprises adding to these compounds at least one photoinitiator of the formula I in which $R_{11}$ and $R_{14}$ are $C_1$–$C_4$alkyl and $R_{12}$ and $R_{13}$ are hydrogen, $C_1$–$C_4$alkyl, $C_1$–$C_4$alkoxy or chlorine and irradiating the compositions with daylight and/or daylight-equivalent light sources.

Preferred compounds for this use or this method are compounds of the formula I in which Z is oxygen, $R_{11}$ and $R_{14}$ are methyl and $R_{12}$ and $R_{13}$ are hydrogen or methyl.

The invention likewise relates to the use of compounds of the formula I in which $R_{11}$ and $R_{14}$ are $C_1$–$C_4$alkyl and $R_{12}$ and $R_{13}$ are hydrogen, $C_1$–$C_4$alkyl, $C_1$–$C_4$alkoxy or chlorine for the curing of shaped articles made from composite compositions, and to a method of curing shaped articles made from composite compositions using the above-defined compounds of the formula I.

The invention also relates to the use of the composition according to the invention for the production of coating substances, in particular white paints for wood coatings and metal coatings, or clear coating materials, for the production of coating materials pigmented with coloured pigments, for the production of clear or pigmented aqueous dispersions, for the production of printing inks, for the production of powder coatings, for the production of three-dimensional articles by bulk curing or stereolithography, for the production of dental filling compositions, for the production of printing plates, for the production of masks for screen printing, for the production of photoresists for printed electronic circuits, for the production of adhesives, as a coating for optical fibres or as a coating or encapsulation of electronic components.

The invention additionally relates to a method for the photopolymerization of compounds containing ethylenically unsaturated double bonds, which comprises irradiating a composition as described above with light in the range from 200 to 600 nm.

In accordance with the invention this method is also used for the production of coating substances, especially white paints for wood coatings and metal coatings, or clear coating materials, for the production of coating materials which are pigmented with colour pigments, for the production of clear or pigmented aqueous dispersions, for the production of printing inks, for the production of powder coatings, for the production of coating substances for daylight-curable constructional coatings and road markings, for the production of dental filling compositions, for the production of printing plates, for the production of masks for screen printing, for the production of photoresists for printed electronic circuits, for the production of adhesives, for the production of coatings for optical fibres, for the production of coatings or encapsulations of electronic components, and in the method of bulk curing or stereolithography.

The invention likewise relates to a coated substrate which is coated on at least one surface with a composition as described above, and to a process for the photographic production of relief images in which a coated substrate is subjected to imagewise exposure and then the unexposed areas are removed with a solvent.

The examples which follow illustrate the invention in more detail. As in the remainder of the description and the patent claims, parts and percentages are by weight unless stated otherwise.

EXAMPLE 1

(method A): Preparation of 1,10-bis [bis(2,4,6-trimethylbenzoyl)phosphine oxide]decane 156.4 ml (0.25 mol) of 1.6M butyllithium are added dropwise over the course of 30 minutes at 0° C., under a nitrogen atmosphere, to a solution of 25.3 g (0.25 mol) of diisopropylamine in 100 ml of tetrahydrofuran (THF). At from −20° to 30° C., this solution is added dropwise to a solution of 45.7 g (0.25 mol) of 2,4,6-trimethylbenzoyl chloride and 12.9 g (0.0625 mol) of 1,10-bis(phosphino) decane in 200 ml of THF. The mixture is stirred at −30° C. for 2 hours and then the yellow solution is allowed to heat up to room temperature and is washed once with water. The organic phase is dried over magnesium sulfate, filtered and concentrated on a rotary evaporator. The residue is dissolved in 200 ml of toluene, and 14.2 g (0.125 mol) of 30% strength hydrogen peroxide are added. The reaction mixture is stirred at 50° C. for 2 hours and then washed with water and saturated sodium hydrogen carbonate solution, dried over magnesium sulfate, filtered and concentrated on a rotary evaporator. Purification by means of chromatography (eluent: hexane/ethyl acetate 3:1) and subsequent recrystallization from hexane gives 16. 1 g (31.3 % of theory) of the title compound as a yellow powder having a melting point of 94°–95° C.

Elemental analysis: calc.: C: 73.15% found: C: 73.03% H: 7.61% H: 7.68%

EXAMPLE 2

(method B): Preparation of 1,6-bis[bis(2,6-dimethoxybenzoyl)phosphine oxide]hexane A mixture of 6.8 g (0.045 mol, 50% strength in toluene) of 1,6-bis(phosphino)hexane and 18.2 g (0.18 mol) of triethylamine is added dropwise at 90°–100° C. to a solution of 36.0 g (0.18 mol) of 2,6-dimethoxybenzoyl chloride in 400 ml of toluene. The mixture is stirred at 90°–100° C. for 6 hours and then the suspension formed is left to cool to room temperature, diluted with toluene and washed once with water and once with sodium bicarbonate solution. 10.2 g (0.09 mol) of 30% strength hydrogen peroxide are added to the organic phase, and the mixture is stirred at 60° C. for 2 hours. It is then washed with water and saturated sodium bicarbonate solution, dried over magnesium sulfate, filtered and concentrated on a rotary evaporator. Crystallization from ethyl acetate gives 10.9 g (28.9% of theory) of the title compound as a yellow powder having a melting point of 219°–220° C.

Elemental analysis: calc.: C: 60.14% found: C: 59.37% H: 5.77% H: 5.83%

EXAMPLES 3–7

The compounds of Examples 3–7 are prepared according to method A or B described above.

The compounds, the respective preparation method and physical data are reproduced in Table 1 below.

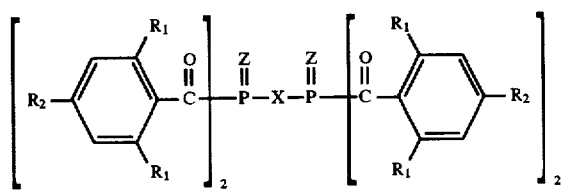

TABLE 1

| Ex. | $R_1$ | $R_2$ | X | Z | Preparation | Melting point [°C.] | Elemental analysis [%] calc. found C | H |
|---|---|---|---|---|---|---|---|---|
| 1 | $CH_3$ | $CH_3$ | $-(CH_2)_{10}-$ | O | A | 94–95 | 73.15 / 73.03 | 7.61 / 7.68 |
| 2 | $OCH_3$ | H | $-(CH_2)_6-$ | O | B | 219–220 | 60.14 / 59.37 | 5.77 / 5.83 |
| 3 | $CH_3$ | $CH_3$ | $-(CH_2)_2-CH(CH_3)-$ | O | A | 60 | 71.53 | 7.09 |

TABLE 1-continued

| Ex. | R₁ | R₂ | X | Z | Preparation | Melting point [°C] | Elemental analysis [%] calc. / found C | H |
|---|---|---|---|---|---|---|---|---|
| 4 | OCH₃ | H | (phenyl) | S | A | 126 | 71.10 / 58.47 / 58.21 | 7.06 / 4.67 / 5.15 |
| 5 | CH₃ | CH₃ | —CH₂—(phenyl)—CH₂— | O | A | 70 | 73.27 / 72.90 | 6.66 / 7.10 |
| 6 | Cl | H | —CH₂—(phenyl)—CH₂— | O | A, B | 187 | 48.36 / 48.45 | 2.25 / 2.50 |
| 7 | CH₃ | CH₃ | —CH₂—(cyclohexyl)—CH₂— | O | A | 181 | 72.71 / 72.52 | 7.37 / 7.39 |

EXAMPLE 8

Reactivity in a polyester acrylate white paint
A UV-curable white paint is prepared by mixing

- 67.5 parts of polyester acrylate oligomer (®Ebecryl 830, UCB, Belgium)
- 5.0 parts of hexanediol diacrylate
- 2.5 parts of trimethylolpropane triacrylate
- 25.0 parts of rutile titanium dioxide (®R-TC2, Tioxide, France)

The compounds according to the invention which are to be tested are incorporated into this formulation at a concentration of 2% by weight.

The paint is applied to a coil-coated aluminium panel using a 100 μm slotted doctor knife and then cured. Curing is carried out by conveying the sample, on a conveyor belt which moves at a speed of 10 m/min, beneath a 80 W/cm medium-pressure mercury lamp (Hanovia, U.S.A.). The number of passages which are necessary to reach a smearproof state is determined. The König pendulum hardness (DIN 53157) is then determined in [s]. The pendulum hardness is a measure of the through-curing of the composition. The higher the values, the more effective the curing which has been carried out. After the first determination of pendulum hardness, the coating was after-exposed under 6 lamps of the type TL 40W/03 (Philips; emission maximum at 430 nm) and after 15 minutes the pendulum hardness was determined again. The result is shown in Table 2.

TABLE 2

| Comp. from Example | Smearproof [x · 10 m/min] | Pendulum hardness immed. | after 15 min |
|---|---|---|---|
| 1 | 2 | 113 | 163 |
| 3 | 3 | 118 | 146 |
| 5 | 3 | 118 | 133 |

EXAMPLE 9

Reactivity in a polyester acrylate white paint

The test method of Example 8 is repeated. The photoinitiator incorporated, however, is a mixture of 75% 1-benzoyl-1-hydroxy-1-methylethane and 25% compound of Example 1. The results can be taken from Table 3.

TABLE 3

| Smearproof [x · 10 m/min] | Pendulum hardness immed. | after 15 min |
|---|---|---|
| 1 | 68 | 132 |

EXAMPLE 10

Curing of a white paint

A white paint is prepared from 75 parts of a formulation of:

- 99.5% of ®Roskydal UV 502 A (solution of an unsaturated polyester in styrene, Bayer)
- 0.5% of ®Byk 300 (levelling assistant, Byk-Mallinckrodt)
- 25.0% of ®R-TC2 (titanium dioxide, Tioxide)

The photoinitiator of Example 1 is incorporated in this formulation at a concentration of 2% by weight. The formulation is applied to chipboards using a 150 μm slotted doctor knife. Prior to curing, the coated boards are stored at 22° C. for one minute. They are then cured at a belt speed of 6 m/min or 3 m/min under a lamp combination of one 120 W/cm fusion D and one 80 W/cm medium-pressure mercury lamp (Hanovia, U.S.A.). The König pendulum hardness is then determined. The results are listed in Table 4.

TABLE 4

| | Pendulum hardness after | |
|---|---|---|
| curing at 6 m/min | | curing at 3 m/min |
| 62 | | 110 |

EXAMPLE 11

Curing of a white paint

2% by weight of a mixture comprising 75% of 1-benzoyl-1-hydroxy-1-methylethane and 25% of the compound of Example 1 are incorporated as photoinitiator into the formulation as described in Example 10. The formulation is applied to chipboards using a 150 μm slotted doctor knife. Prior to curing the coated board is stored at 22° C. for 1.5 min and is then cured at a belt speed of 3 m/min under a lamp combination of one 120 W/cm fusion D and one 80 W/cm medium-pressure mercury lamp (Hanovia, U.S.A.). The subsequent assimilation of the König pendulum hardness gives a value of 61 s.

EXAMPLE 12

Curing of a white paint using sunlight

The composition described in Example 10 is applied to chipboards using a 150 μm slotted doctor knife and is exposed to sunlight. A tack-free surface is obtained after 10 minutes.

EXAMPLE 13

Curing of shaped parts made from a composite composition

A formulation is prepared from 98.0 parts of unsaturated polyester/styrene Roskydal 500A (Bayer, Germany)

1.5 parts of 1-benzoyl-1-hydroxy-1-methylethane ®Darocur 1173 (Ciba, Switzerland)

0.5 part of the photoinitiator (1) according to the invention from Example 1, (2) from Example 3 and (3) from Example 5

A relatively loose glass fibre fabric as matrix material is fitted into a tubular mould with a diameter of 9 cm and is impregnated with the formulation. The weight ratio of glass fibre fabric to formulation is 1:2. Full curing is effected by irradiation with a Philips TL 40 W03 lamp. Shaped parts of high mechanical stability and stability under load are obtained.

We claim:

1. A compound of the formula I

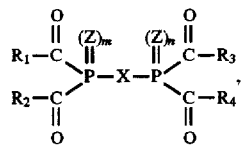

in which

Z is oxygen or sulfur, n and m are independently of one another 0 or 1, $R_1$, $R_2$, $R_3$ and $R_4$ independently of one another are $C_1$-$C_{20}$alkyl, cyclopropyl, cyclopentyl, cyclohexyl, $C_2$-$C_8$alkenyl, phenyl which is unsubstituted or is substituted one to four times by $C_1$-$C_{12}$alkyl, $C_1$-$C_{12}$alkoxy, $C_1$-$C_6$alkylthio and/or halogen, naphthyl which is unsubstituted or is substituted one to four times by $C_1$-$C_{12}$alkyl, $C_1$-$C_{12}$alkoxy, $C_1$-$C_6$alkylthio and/or halogen, biphenyl which is unsubstituted or is substituted one to four times by $C_1$-$C_{12}$alkyl, $C_1$-$C_{12}$alkoxy, $C_1$-$C_6$alkylthio and/or halogen, or $R_1$, $R_2$, $R_3$ and $R_4$ independently of one another are a 5- or 6-membered heterocyclic ring which contains O, S or N, or $R_1$ and $R_2$ or/and $R_3$ and $R_4$ are linked to form a ring containing 4 to 10 carbon atoms which is unsubstituted or is substituted by 1 to 6 $C_1$-$C_4$alkyl groups, X is linear or branched $C_1$-$C_{18}$alkylene, is $C_2$-$C_{18}$alkylene which is interrupted one or more times by —O—, —S—, —NR$_5$—, —P(O)R$_6$— or —SO$_2$—, or is $C_1$-$C_6$alkylene which is substituted by Cl, F, $C_1$-$C_4$alkoxy, COOR$_7$, phenyl, $C_1$-$C_4$alkylphenyl, $C_1$-$C_4$alkylnaphthyl, phenyl-$C_1$-$C_4$alkyl, naphthyl-$C_1$-$C_4$alkyl, phenyl-$C_1$-$C_4$alkoxy, naphthyl-$C_1$-$C_4$alkoxy, $C_1$-$C_4$alkoxy-$C_1$-$C_4$alkoxy and/or CN, or X is $C_2$-$C_8$alkylene which is substituted by one or two groups of the formula G

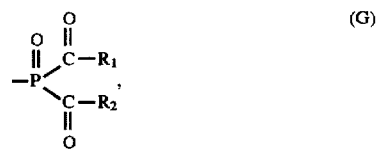

or X is a group of the formula (II),

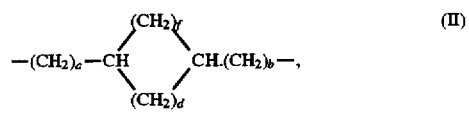

in which a and b independently of one another are 0 or 1, the sum of d and f is 3 to 8, with neither d nor f being 0, or X is a group —CH$_2$—CH=CH—CH$_2$— or —CH$_2$—C≡C—CH$_2$—, or X is xylylene,

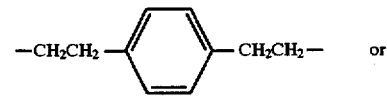 or

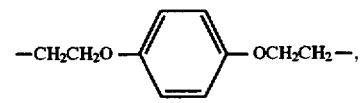

or X is a group of the formula (XII), or (XIV),

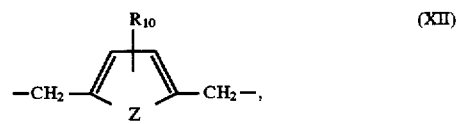

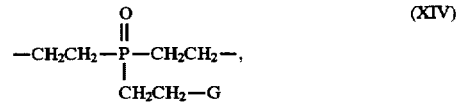

in which

Z and G are as defined above and

Y is a single bond, —CR$_8$R$_9$—, —O—, —NR$_5$—, —S—, —SO$_2$—, —(CH$_2$)$_p$— or —CH=CH—, p is a number from 2 to 12, $R_5$ is hydrogen, $C_1$-$C_{12}$alkyl or phenyl, $R_6$ is $C_1$-$C_4$alkyl or phenyl, $R_7$ is $C_1$-$C_{12}$alkyl, $C_2$-$C_{18}$alkyl which is interrupted by one or more O atoms, or is benzyl, phenyl, cyclopentyl or cyclohexyl, and $R_8$ is hydrogen, methyl or ethyl, $R_9$ is hydrogen or $C_1C_4$alkyl, and $R_{10}$ is hydrogen $C_1$-$C_4$alkyl, $C_1$-$C_4$alkoxy or halogen.

2. A compound of the formula I according to claim 1, in which $R_1$, $R_2$, $R_3$ and $R_4$ are tert-$C_4$-$C_8$alkyl, cyclopentyl, cyclohexyl or a radical

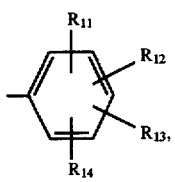

in which $R_{11}$ is $C_1$-$C_8$alkyl, $C_1$-$C_8$alkoxy, $C_1$-$C_4$alkylthio or halogen, $R_{12}$, $R_{13}$ and $R_{14}$ independently of one another are hydrogen, $C_1$-$C_8$alkyl, $C_1$-$C_8$alkoxy, $C_1$-$C_4$alkylthio or halogen, or $R_1$, $R_2$, $R_3$ and $R_4$ are naphthyl which is unsubstituted or is substituted one to four times by $C_1$-$C_8$alkyl, $C_1$-$C_8$alkoxy, $C_1$-$C_4$alkylthio and/or halogen, or are biphenyl which is unsubstituted or is substituted one to four times by $C_1$-$C_8$alkyl, $C_1$-$C_8$alkoxy, $C_1$-$C_4$alkylthio and/or halogen, or $R_1$, $R_2$, $R_3$ and $R_4$ independently of one another are a 5- or 6-membered heterocyclic ring containing O, S or N, or $R_1$ and $R_2$ and $R_3$ and $R_4$ are linked to form a benzene ring, in which case $R_1$ and $R_2$, and $R_3$ and $R_4$, are in each case ortho to one another, X is linear or branched $C_1$-$C_{18}$alkylene, is $C_4$-$C_{18}$alkylene which is interrupted one or more times by —O—, —S— or —SO$_2$—, or is $C_1$-$C_4$alkylene which is substituted by Cl, F, methoxy, COOCH$_3$, phenyl, $C_1$-$C_4$alkyl-phenyl or phenyl-$C_1$-$C_4$alkyl, or X is $C_2$-$C_8$alkylene which is substituted by one or two groups of the formula G, or X is a group of the formula (II), or X is a group —CH$_2$—CH=CH—CH$_2$— or —CH$_2$—C≡C—CH$_2$—, or is xylylene,

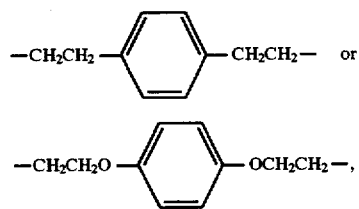

or X is a group of the formula (XIV),

Y is a single bond, —CR$_8$R$_9$—, —O—, —S—, —SO$_2$—, —CH$_2$CH$_2$— or —CH=CH— and $R_8$ and $R_9$ independently of one another are hydrogen or methyl.

3. A compound of the formula I according to claim 1, in which $R_1$, $R_2$, $R_3$ and $R_4$ are a radical

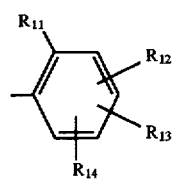

$R_{11}$ is $C_1$-$C_4$alkyl, $C_1$-$C_1$-$C_4$alkoxy, $C_1$-$C_4$alkylthio or halogen, $R_{12}$, $R_{13}$ and $R_{14}$ independently of one another are hydrogen, $C_1$-$C_4$alkyl, $C_1$-$C_4$alkoxy, $C_1$-$C_4$alkylthio or halogen, or $R_1$, $R_2$, $R_3$ and $R_4$ are naphthyl which is unsubstituted or is substituted one to four times by $C_1$-$C_4$alkyl, $C_1$-$C_4$alkoxy, $C_1$-$C_2$alkylthio and/or halogen, or are biphenyl which is unsubstituted or is substituted one to four times by $C_1$-$C_4$alkyl, $C_1$-$C_4$alkoxy, $C_1$-$C_2$alkylthio and/or halogen, X is linear or branched $C_1$-$C_{12}$alkylene, or is $C_4$-$C_{18}$alkylene which is interrupted one or more times by —O— or —S—, or is $C_1$-$C_4$alkylene which is substituted by Cl, F, methoxy, phenyl or benzyl, or X is $C_2$C$_8$alkylene which is substituted by one or two groups of the formula G or X is a group

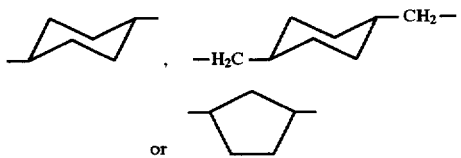

or X is a group —CH$_2$—CH=CH—CH$_2$—, or is xylylene, or X is a group of the formula (XIV), Y is a single bond, —CR$_8$R$_9$—, —O—, —S— or —CH$_2$CH$_2$—, and $R_8$ and $R_9$ independently of one another are hydrogen or methyl.

4. A compound of the formula I according to claim 1, in which $R_1$, $R_2$, $R_3$ and $R_4$ are a radical,

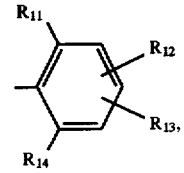

in which $R_{11}$ and $R_{14}$ independently of one another are $C_1$-$C_4$alkyl, $C_1$-$C_4$alkoxy, $C_1$-$C_2$alkylthio or halogen, $R_{12}$ and $R_{13}$ independently of one another are hydrogen, $C_1$-$C_4$alkyl, $C_1$-$C_4$alkoxy, $C_1$-$C_2$alkylthio or halogen, X is linear or branched $C_1$-$C_{12}$alkylene, $C_4$-$C_{14}$alkylene which is interrupted one or more times by —O— or —S—, or $C_2$-$C_8$alkylene which is substituted by one or two groups of the formula G, or is a group

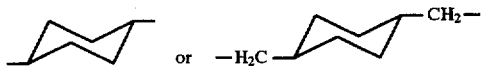 or X is a group —CH₂—CH=CH—CH₂—, or xylylene or X is a group of the formula (XIV), Y is a single bond or —CR₈R₉—, and R₈ and R₉ independently of one another are hydrogen or methyl.

5. A compound of the formula I according to claim 1, in which

R₁, R₂, R₃ and R₄ are a group of the formula

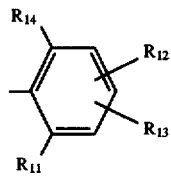

in which

R₁₁ and R₁₄ independently of one another are C₁–C₄alkyl, methoxy or chlorine,

R₁₂ and R₁₃ independently of one another are C₁–C₄alkyl, C₁–C₄alkoxy, chlorine or hydrogen, X is linear or branched C₁–C₁₂alkylene, C₄–C₁₈alkylene which is interrupted one or more times by —O—, or C₃–C₆alkylene which is substituted by one or two groups of the formula G, or X is a group —CH₂—CH=CH—CH₂— or X is a group

6. A compound of the formula I according to claim 5, in which

R₁₂ is hydrogen and

X is linear or branched C₁–C₁₂alkylene, C₄–C₁₈alkylene which is interrupted one or more times by —O—, or C₃–C₆alkylene which is substituted by one or two groups of the formula G, or X is a group —CH₂—CH=CH—CH₂—, xylylene.

7. A compound of the formula I according to claim 6, in which

X is linear or branched C₁–C₁₂alkylene or C₄–C₁₈alkylene which is interrupted one or more times by —O—, or X is a group —CH₂—CH=CH—CH₂—, xylylene or X is

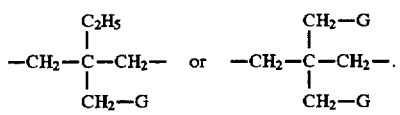

8. A compound according to claim 1, in which R₁, R₂, R₃ and R₄ are identical.

9. A compound according to claim 1, in which Z is oxygen and n and m are 1.

10. A compound according to claim 1, in which

Z is oxygen, n and m are 1,

R₁, R₂, R₃ and R₄ are identical and are phenyl which is disubstituted or trisubstituted by methyl, chlorine or methoxy, and X is C₄–C₁₂alkylene,

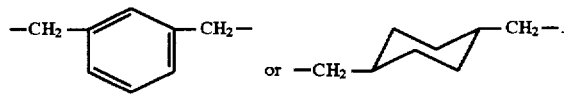

* * * * *